(12) United States Patent
Tandon et al.

(10) Patent No.: US 10,488,390 B2
(45) Date of Patent: Nov. 26, 2019

(54) SYSTEM AND METHOD FOR HIGH-THROUGHPUT ASSESSMENT OF CELLULAR CARDIOTOXICITY, DRUG SCREENING, AND CARDIOGENIC FACTORS VIA ONLINE PHYSIOLOGICAL MEASUREMENTS

(71) Applicant: THE TRUSTEES COLUMBIA UNIVERSITY IN THE CITY OF NEW YORK, New York, NY (US)

(72) Inventors: Nina Tandon, New York, NY (US); Elisa Cimetta, Long Island City, NY (US); Kacey Ronaldson, Midlothian, VA (US); Gordana Vunjak-Novakovic, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 535 days.

(21) Appl. No.: 14/902,238

(22) PCT Filed: Jul. 2, 2014

(86) PCT No.: PCT/US2014/045265
§ 371 (c)(1),
(2) Date: Dec. 30, 2015

(87) PCT Pub. No.: WO2015/003064
PCT Pub. Date: Jan. 8, 2015

(65) Prior Publication Data
US 2016/0131636 A1     May 12, 2016

Related U.S. Application Data

(60) Provisional application No. 61/903,126, filed on Nov. 12, 2013, provisional application No. 61/842,559, filed on Jul. 3, 2013.

(51) Int. Cl.
*G01N 33/483* (2006.01)
*G01N 27/07* (2006.01)
(Continued)

(52) U.S. Cl.
CPC ......... *G01N 33/4836* (2013.01); *G01N 27/26* (2013.01); *G01N 33/5008* (2013.01)

(58) Field of Classification Search
None
See application file for complete search history.

(56) References Cited

U.S. PATENT DOCUMENTS 5,563,067 A     10/1996  Sugihara
9,290,756 B2 *   3/2016  Ross ...................... C12N 13/00
(Continued)

FOREIGN PATENT DOCUMENTS

WO     2012/043820 A1     4/2012

OTHER PUBLICATIONS

International Search Report for PCT/US2014/045265 dated Jan. 21, 2015. 3 pages.

*Primary Examiner* — Kathryn Wright
(74) *Attorney, Agent, or Firm* — Walter M. Egbert, III; Matthew S. Gibson; Reed Smith LLP

(57) ABSTRACT

An integrated system for detecting safety and/or efficacy issues related to potential drug compounds by combining tissue maturation, imaging and electrophysiology measurements, at high throughput, with high signal to noise ratio. Testing includes cardiotoxicity screening, drug screening, and screening for cardiogenic factors via on-line physiological measurements.

25 Claims, 41 Drawing Sheets

(51) Int. Cl.
*G01N 27/26* (2006.01)
*G01N 33/50* (2006.01)

(56) References Cited

U.S. PATENT DOCUMENTS

| | | | |
|---|---|---|---|
| 2006/0057771 A1 | 3/2006 | Kovacs | |
| 2008/0113352 A1 | 5/2008 | Voros | |
| 2009/0322309 A1* | 12/2009 | Zhu | G01N 33/4836 |
| | | | 324/71.1 |
| 2010/0120626 A1* | 5/2010 | Ross | C12N 13/00 |
| | | | 506/7 |
| 2010/0197524 A1 | 8/2010 | Janata | |
| 2012/0164117 A1 | 6/2012 | Gepstein | |
| 2012/0178335 A1 | 7/2012 | Eden | |

* cited by examiner

SYSTEM AND METHOD FOR HIGH-THROUGHPUT ASSESSMENT OF CELLULAR CARDIOTOXICITY, DRUG SCREENING, AND CARDIOGENIC FACTORS VIA ONLINE PHYSIOLOGICAL MEASUREMENTS

CROSS-REFERENCE TO RELATED APPLICATIONS

This application claims the benefit of U.S. Provisional Application No. 61/842,559, filed Jul. 3, 2013 and claims the benefit of U.S. Provisional Application No. 61/903,126, filed Nov. 12, 2013.

STATEMENT OF GOVERNMENT INTEREST

This invention was made with government support under grant EB002520 awarded by the National Institutes of Health. The Government has certain rights in this invention.

BACKGROUND OF THE DISCLOSED SUBJECT MATTER

Field of the Disclosed Subject Matter

The disclosed subject matter relates to a system and method for high-throughput assessment of cellular cardiotoxicity, drug screening, and cardiogenic factors via online physiological measurements. Particularly, the presently disclosed subject matter relates to a microelectrode array that reduces signal noise and isolates signal acquisition from transmission and processing noise, an optically transparent platform for cell culture that allows for simultaneous electrical and optical data acquisition, and a method of microelectrode array fabrication that enables control of patterned cells and their respective patterned electrodes.

Background

The average cost of bringing a new drug to market is $1.3 billion dollars. It has been estimated that to end up with one drug in the market, it is necessary to screen about five to ten thousand compounds, which are then whittled away through preclinical and clinical testing for safety and efficacy to treat a particular disease. Most compounds are abandoned before testing in man, and only the best, most active and most likely not to cause harm move into the clinical phase of drug development as the lead compound, although one or two other compounds may be developed in parallel as a back-up compound.

As a compound goes through clinical trials the probability that it will eventually gain approval for marketing is quite low. In 2011, the latest probabilities of success relating to the start of a clinical phase in a drug's development, were:

| Clinical Trial Phase | Probability of Success |
|---|---|
| Phase 1 | 63% |
| Phase 2 | 33% |
| Phase 3 | 55% |
| Approval | 80% |

Most failures occur by the end of Phase 2 clinical studies, after pharmaceutical companies already invested millions of dollars in a lead drug development compound. Sometimes the back-up compound can be slotted into the development plan, but sometimes it cannot. Accordingly, the high failure rates associated with pharmaceutical development mandate careful decision making during drug development as essential to avoid costly failures.

Cardiotoxicity is a major source of costly, dangerous, late-stage drug failure. Prior methods and systems for evaluating cardiotoxicity of potential drug compounds have been expensive, time-consuming and inaccurate. Such prior methods include conventional microscopy techniques as well as computer based simulation. There is a need for an efficient and economic method and system for screening of potential drug compounds for safety issues such as cardiotoxicity and others, early in the drug development process.

SUMMARY

To achieve these and other advantages and in accordance with the purpose of the disclosed subject matter, as embodied and broadly described, the disclosed subject matter includes a method and system of early detection of safety or efficacy issues associated with drug development compounds.

The system described provides the ability to test a wide range of parameters (e.g., cell source, mechanical, soluble and electrical stimuli) that might impact engineered tissue in a high-throughput manner and in an environment that mimics native heart tissue. This technology presents a means for high-throughput assessment of cellular cardiotoxicity, drug screening, and cardiogenic factors via on-line physiological measurements.

In one embodiment, a system is provided to detect safety and efficacy issues associated with a compound. The system comprises a microelectrode array (MEA) for measuring conduction velocity of cells. The MEA includes a substantially flat substrate having a first surface, such as a glass plate, a plurality of measurement electrodes arrayed on the first surface of the substrate, each electrode having a contact portion and a non-contact portion; and a coating covering a portion of the surface of the substrate and the non-contact portions of the electrodes so as to form a covered region and an uncovered region. The uncovered region defines an annulus.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF EXEMPLARY EMBODIMENTS

In one aspect, a method is provided for efficiently and accurately screening potential therapeutics for safety issues at an early stage of drug development. The method enables a high-throughput, assessment of cellular toxicity, and cardiogenic factors via on-line physiological measurements. The present method is suitable for detection of various cardiac safety factors, including detection of arrhythmia, calcium tracking, and signal propagation velocity. According to another aspect, online monitoring is enabled through a high throughput, integrated system combining tissue maturation, imaging and electrophysiology measurements. Such monitoring is suitable for high-throughput assessment of cellular cardiotoxicity, drug screening, and cardiogenic factors via on-line physiological measurements.

In accordance with one embodiment, micro-patterning techniques can be used to grow cardiac microtissues at relevant size scales and geometries. For example, circular ring patterns can be grown for studies of cardiac arrhythmia, and rectangular strips can be grown for studies of cardiac conduction velocities at widths of 50-100 μm. The patterned microtissues are introduced to a system, described below and embodied herein, which measures conduction velocities and extracellular voltage recordings and calcium fluxes on these patterned microtissues. All measurements can be performed on-line, and in a high-throughput fashion.

In some embodiments, measurements can be used to detect several cardiac safety and efficacy related issues, including: prediction of in vivo cardiotoxicity; identification of promising cardiac therapeutic targets; screening of chemical cardiogenic factors; and screening of therapeutic cells.

As cardiac toxicity is a leading contributor to costly and dangerous drug withdrawal from market, and late-stage attrition, there is an urgent need for in vitro assays capable of early detection of cardiac toxicity issues. The methods and system described provides for a combination of multiple modalities (e.g. electrical activity, conduction velocities, and calcium flux) to assess drug induced cardiac toxicity in an in-vivo-like model (i.e. engineered cardiac microtissues) at sufficient throughput to be a valuable addition to the cardiovascular in vitro screening arsenal.

Cardiomyocytes derived from pluripotent stem cells are attractive to adapt to large scale production processes due to their stability in long-term culture, and relevant physiology. The present disclosure provides for assessment of cardiogenic factors to aid in studies of derivations of cardiomyocytes from stem cell sources.

The present disclosure provides for quality control screening of cells for eventual implantation and/or studies.

Figure 1:
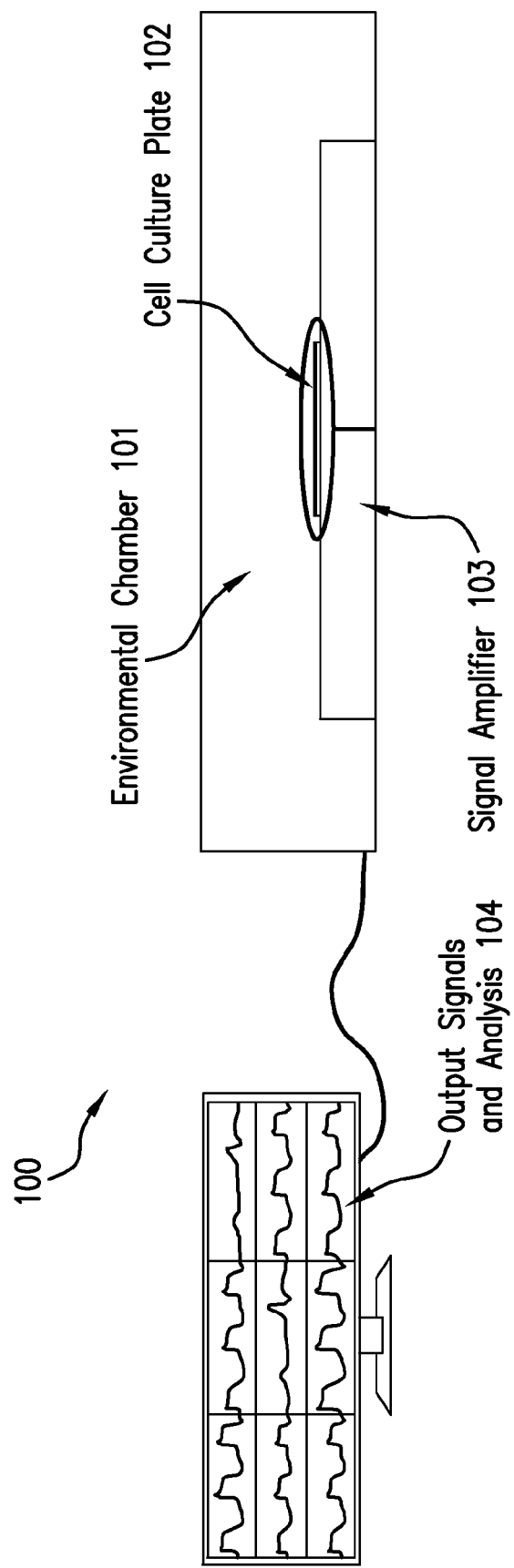
FIG. 1 is a schematic representation of a diagnostic apparatus according to an embodiment of the present subject matter.

In another aspect, a system to evaluate the micropatterned tissue for early detection of safety and efficacy issues in drug compounds is provided (FIG. 1). As schematically shown in FIG. 1, the diagnostic system 100 includes a chamber 101 (e.g., environmental chamber) comprising one or more cell culture plates 102. Cell culture plate 102 may contain cells either cultured in place within the chamber 102 or cultured in advance (e.g., prior to introduction to the environmental chamber). The cell culture plate 102 is operatively engaged to a signal amplifier 103, and makes electrical contact through one or more contact plates (best shown in FIG. 2). An output from signal amplifier 103 is directed to output signal analysis system 104. In some embodiments, signal analysis system 104 is a general purpose computer running signal analysis software. The output signals comprise measurements of voltage.

Figure 2:
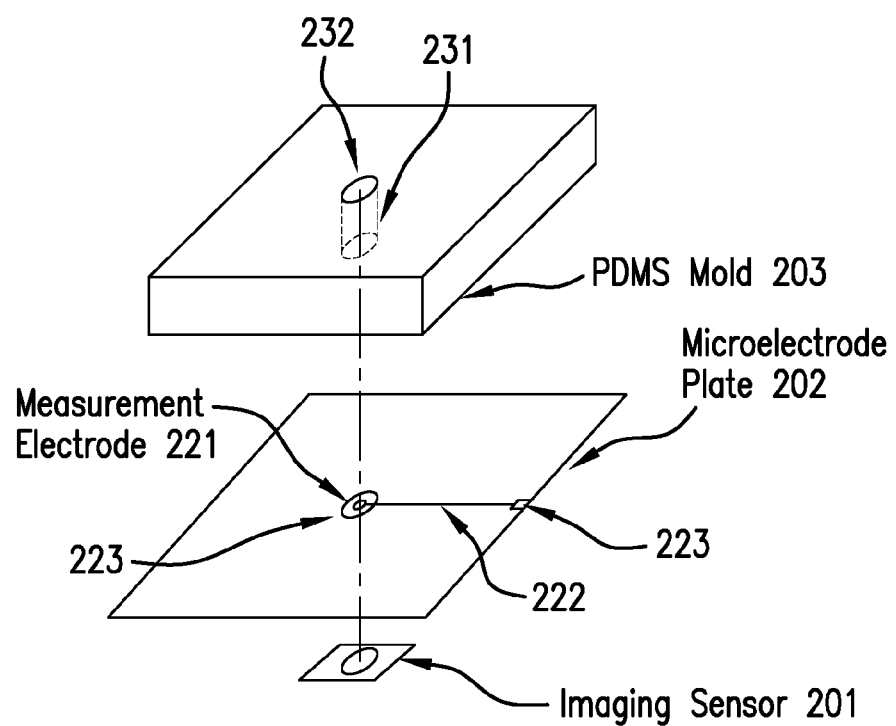
FIG. 2 is a schematic representation of a cell culture plate according to an embodiment of the present subject matter.

Cell culture plate 102, as shown in the expanded view of FIG. 2, may include an imaging sensor 201, a microelectrode plate 202, and mold 203, such as a polydimethylsiloxane (PDMS, or dimethicone) mold. In one embodiment, the microelectrode plate 202 is disposed between the PDMS mold 203 and the imaging sensor 201. In various embodiments, image sensor 201 may be a CCD or a CMOS based sensor. The combination of imaging sensor 201 with microelectrode plate 202 allows action potential to be measured simultaneously optically and electrically from the micropatterned tissue using amplification hardware as discussed below.

The microelectrode plate 202 includes at least one measurement electrode 221 and an output lead 222 connected to contact pad 223. Contact pads 321, 322, 323, 324 are adapted to make electrical contact with signal amplifier 103. The PDMS mold 203 includes at least one cell culture well 231. Cell culture well 231 includes removable cover 232. Cell culture well 231 exposes a region 223 of microelectrode plate 202 through the body of PDMS mold 203.

Figure 3:
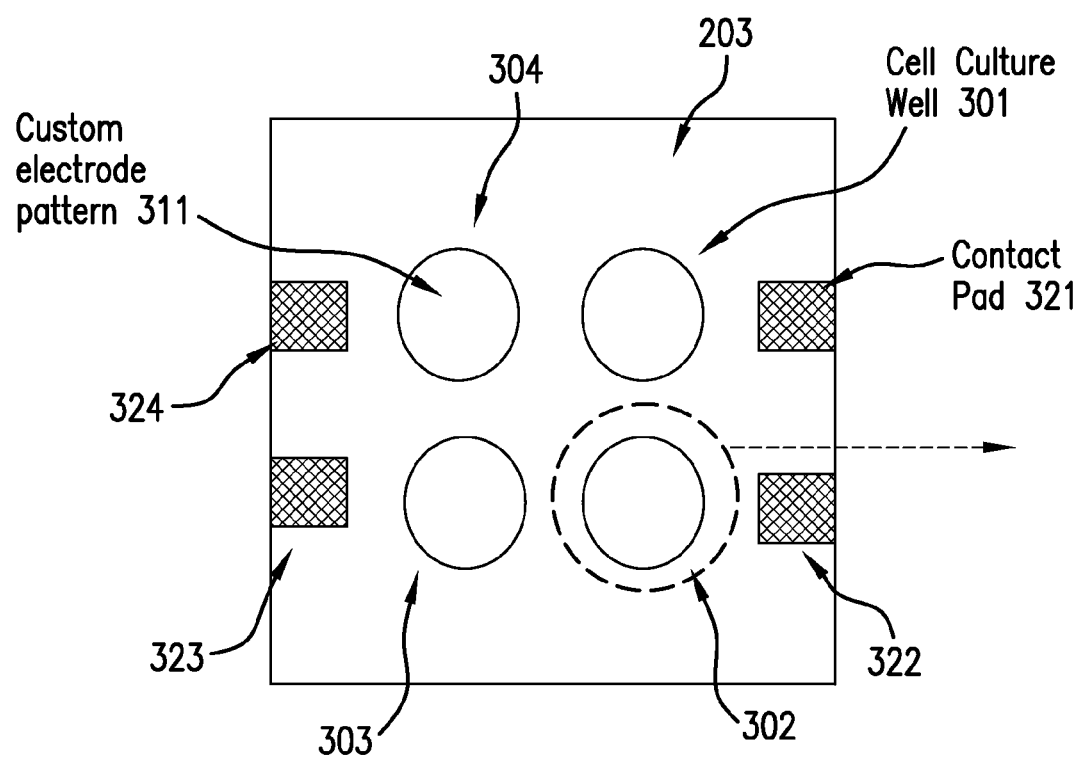
FIG. 3 is a schematic representation of a mold and plate according to an embodiment of the present subject matter.
Figure 4A:
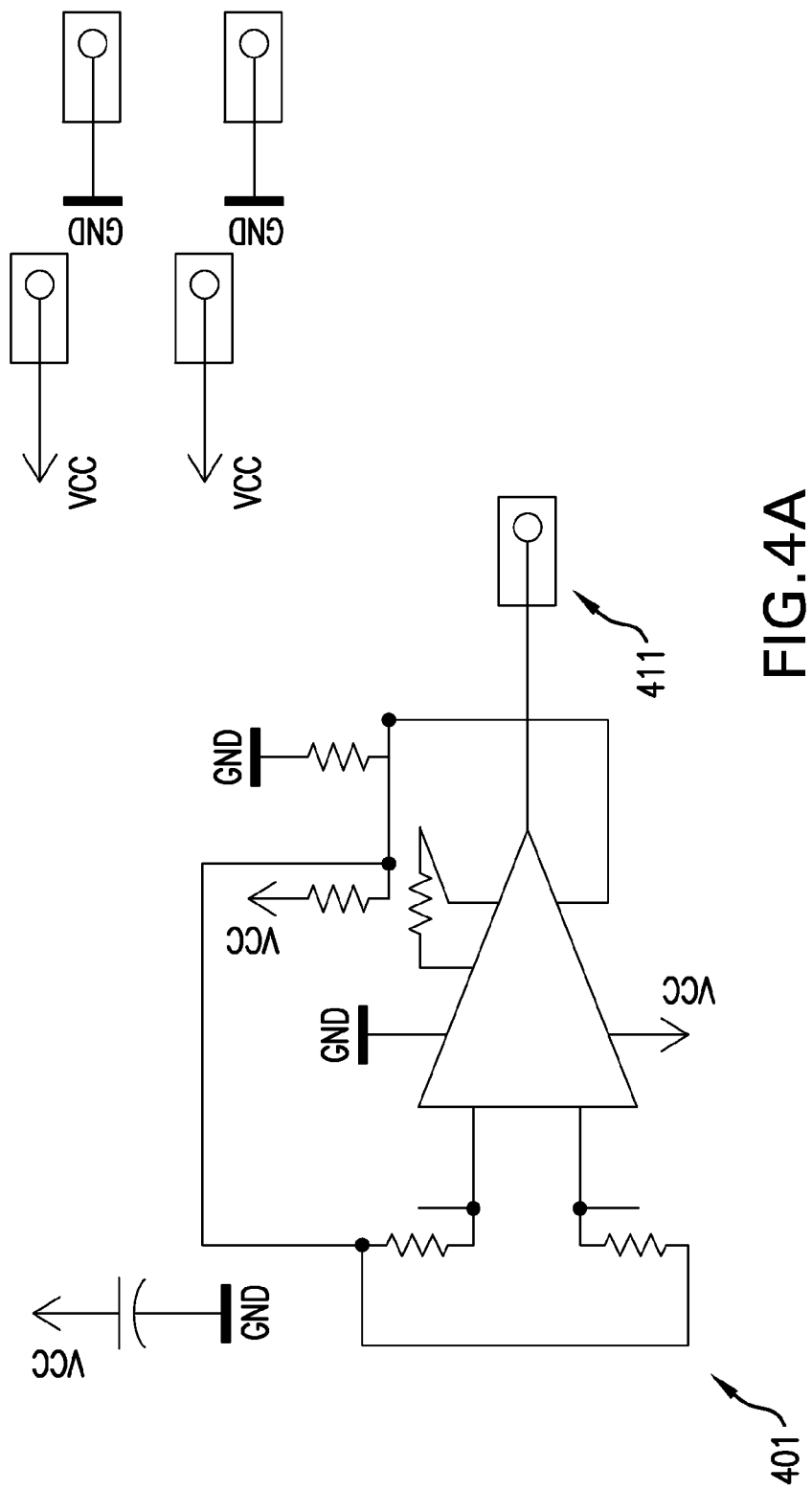
FIGS. 4A-4D are schematic representations of amplifier circuitry board including test circuits according to exemplary embodiments of the present subject matter.
Figure 4B:
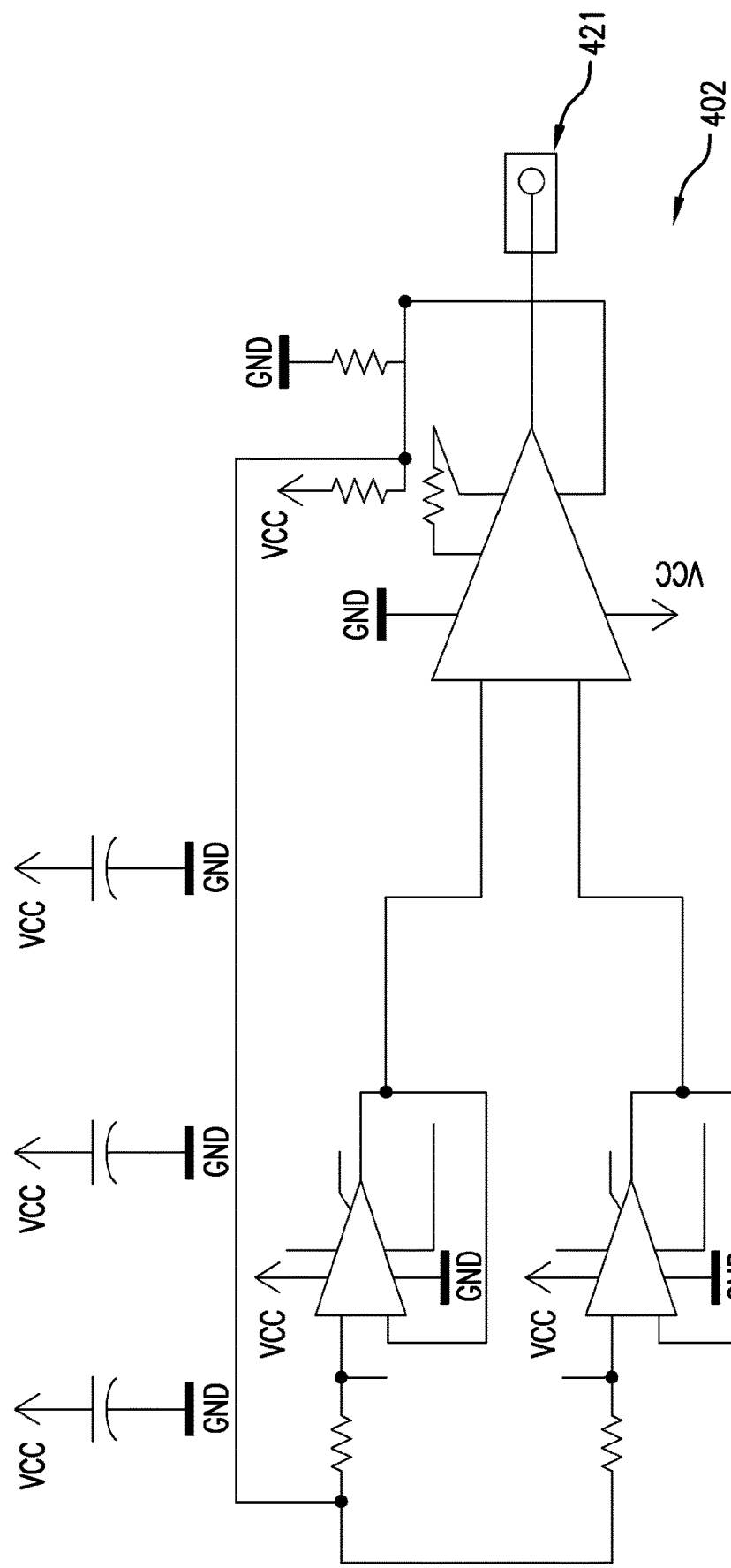
Figure 4C:
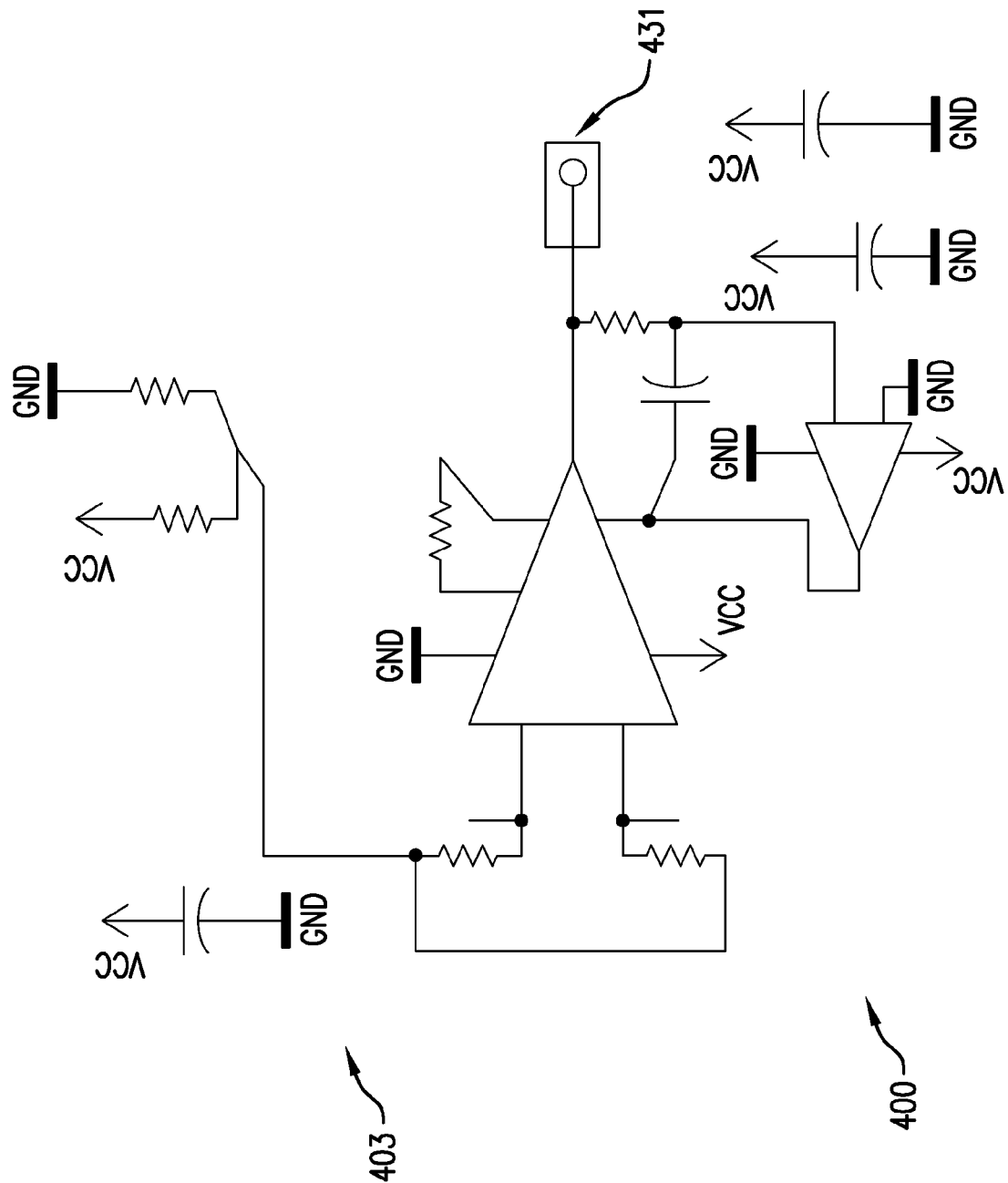
Figure 4D:
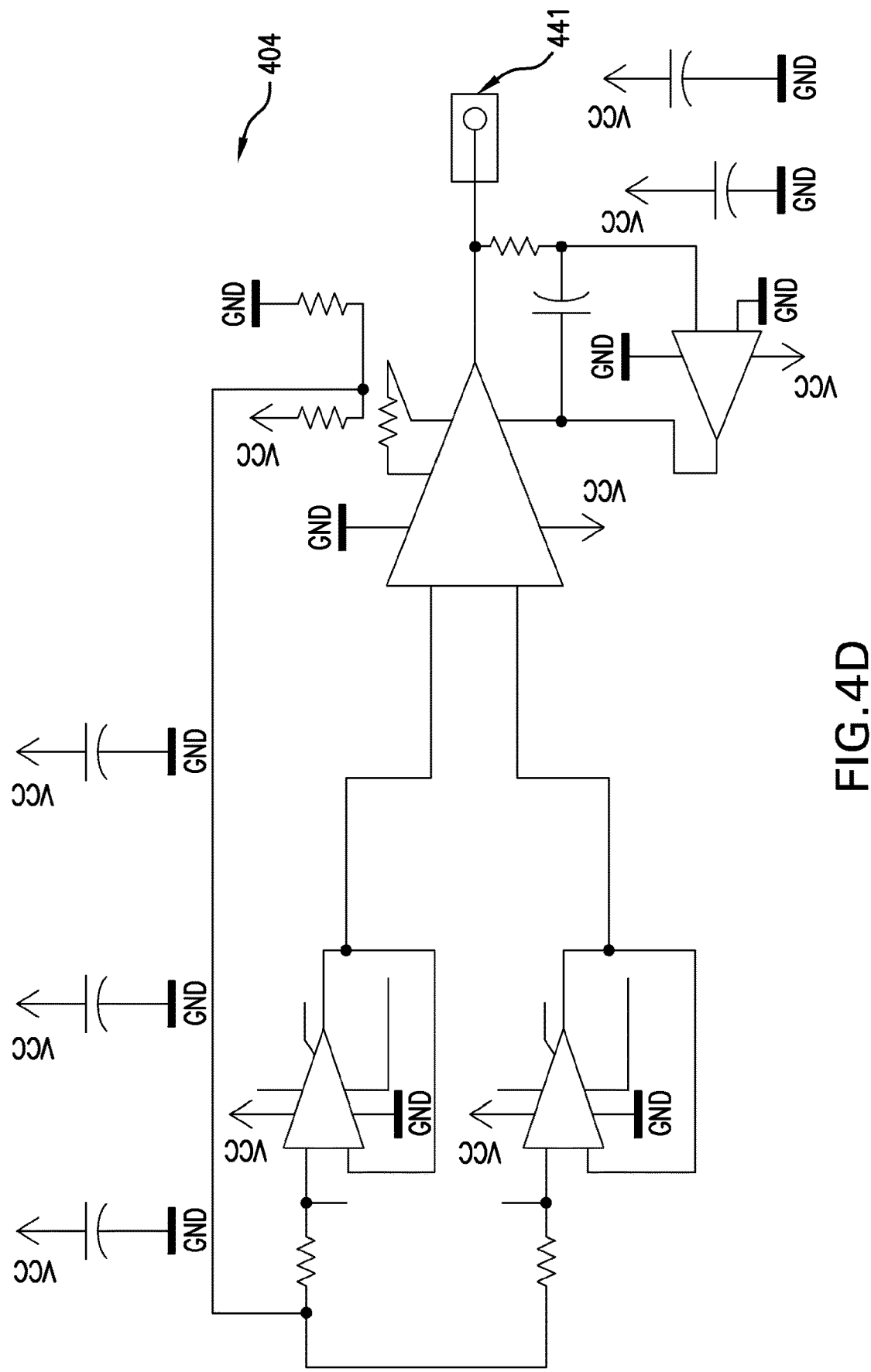

FIG. 3 depicts a top down view of PDMS mold 203 atop microelectrode plate 202. In this example, four cell culture wells 301, 302, 303, and 304 penetrate the body of PDMS mold 203 to expose microelectrode plate 202. Within the areas of microelectrode plate 202 exposed by each cell culture well 301, 302, 303, and 304 are custom electrode patterns 311.

Figure 5:
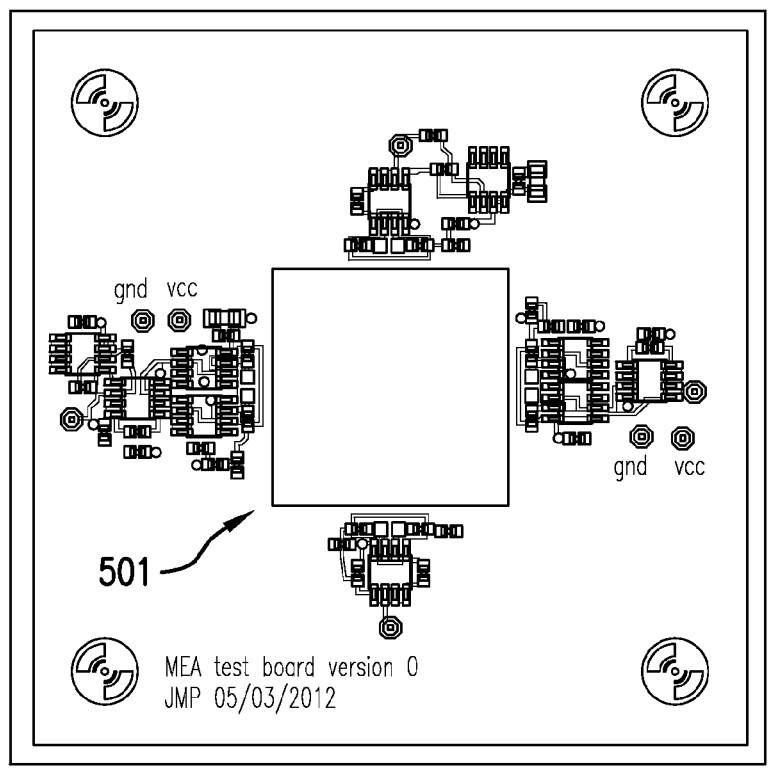
FIG. 5 depicts an exemplary physical layout for an amplifier circuit according to an embodiment of the present subject matter.
Figure 6A:
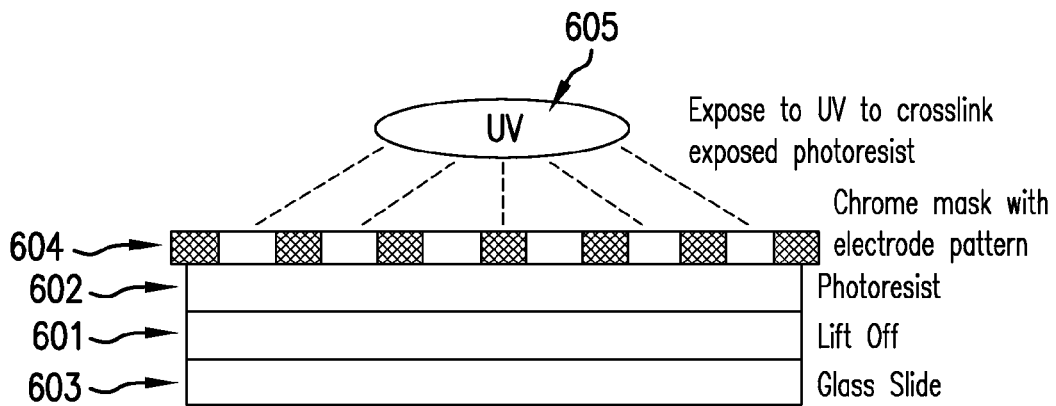
FIGS. 6A-6D illustrate method for fabrication of a microelectrode array according to an exemplary embodiment of the present subject matter.
Figure 6B:
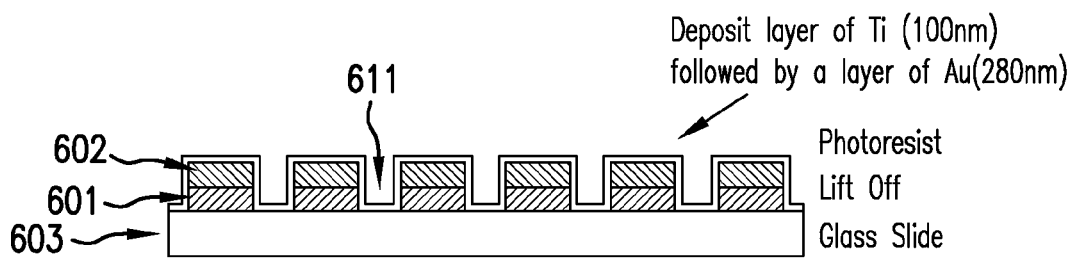
Figure 6C:
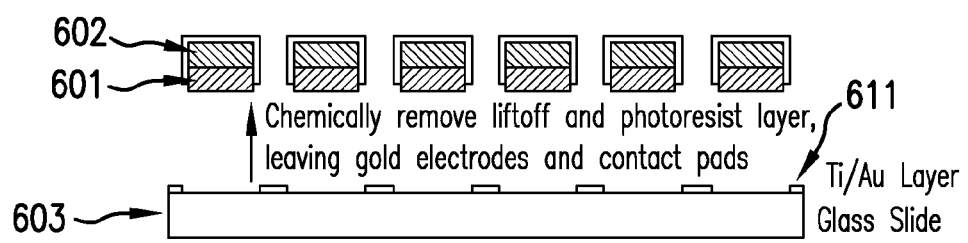
Figure 6D:
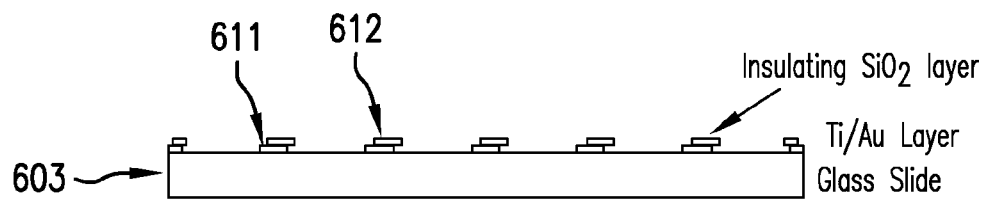

The signal amplifier 103 can embody the design depicted in FIG. 4. As illustrated in FIG. 4, amplifier circuit board 400 can include four test circuits 401, 402, 403, 404. Amplifier circuit board includes links 411, 421, 431, 441, disposed in electrical contact with contacts pads 321, 322, 323, 324 when or if cell culture plate 102 is placed on amplifier 103. In one embodiment, as shown in FIG. 5, amplifier circuit board 400 includes a central region 501 sized to hold cell culture plate 102.

In another aspect, a method for fabricating a microelectrode array in accordance with one embodiment of the disclosed subject matter is provided. As shown in FIG. 6 one embodiment of the method includes a layer of lift-off 601 and a layer of photoresist 602 spun coated onto a glass slide 603. A chrome mask 604 with an electrode pattern is placed over the coated glass slide 603. The coated glass slide 603 is then exposed to ultraviolet light 605 through the chrome mask 604. The UV exposure allows for the crosslinking of regions of photoresist 602 and liftoff 601 according to the electrode design laser-printed on the chrome mask 604.

After UV exposure, a primary adhesion layer of Titanium (Ti) is deposited by Electron Beam Physical Vapor Deposition (electron beam evaporation). In some embodiments, the Titanium layer is about 100 nm thick. A layer of an electroactive metal is then deposited on the Titanium layer to form combined Ti/Au layer 611. In some embodiments, the electroactive metal is gold (Au) and the layer is about 280 nm thick. The layer of electroactive metal 611 will serve as the electrodes of the microelectrode array.

After deposition of layer 611, the photoresist and lift-off layers 602, 601 are chemically removed from glass slide 603. Portions of layer 611 are left behind on glass slide 603 to form patterned electrodes and contact pads.

An insulating layer 612 is then added on top of layer 611. Insulating layer 612 covers only the electrode tracks. In some embodiments, insulating layer 612 is deposited using the same method as is described above for the deposition of layer 611. In such embodiments, insulating layer 612 comprises Silicon dioxide ($SiO_2$ or Silica), and is deposited by Electron Beam Physical Vapor Deposition using a different corresponding complimentary mask design. Although some embodiments use Electron Beam Physical Vapor Deposition as discussed above, alternative methods of deposition such as sputter deposition may be used.

Figure 7:
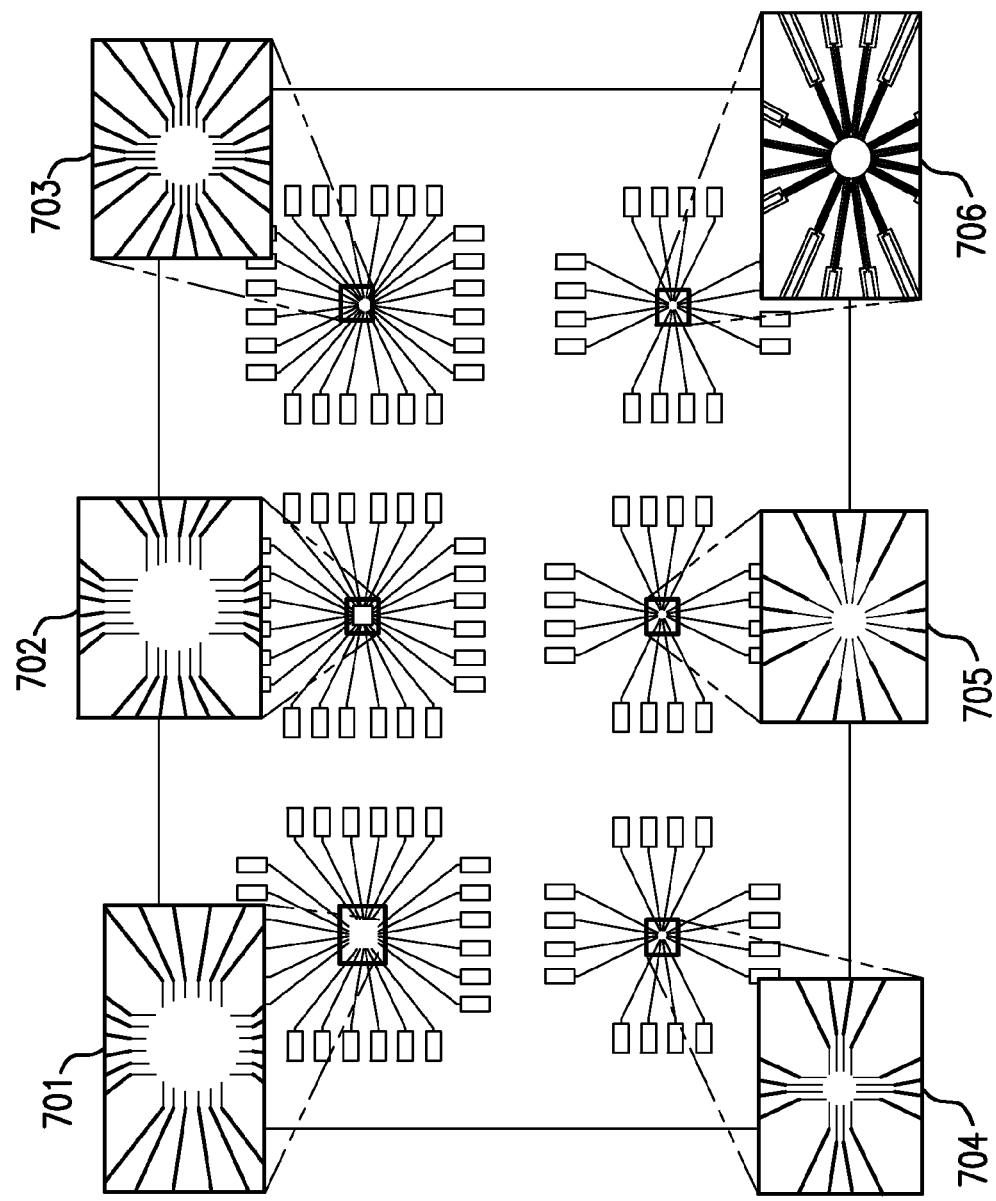
FIG. 7 depicts six exemplary electrode layouts according to an embodiment of the present subject matter.

The fabricated microelectrode array may have various electrode layouts or patterns. For example, FIG. 7 depicts six exemplary electrode layouts of a microelectrode array according to an embodiment of the present disclosure. In some embodiments, layouts 701, 702, 703, 704, 705, 706 are deposited on a glass slide according to the method described with regard to FIG. 6. The ring configuration of these layouts facilitates the study of models of cardiac reentry and arrhythmias. These ring configurations facilitate studies of conduction velocity over time. The closed loop system allows tracking conduction velocity over long periods of time.

Figure 8:
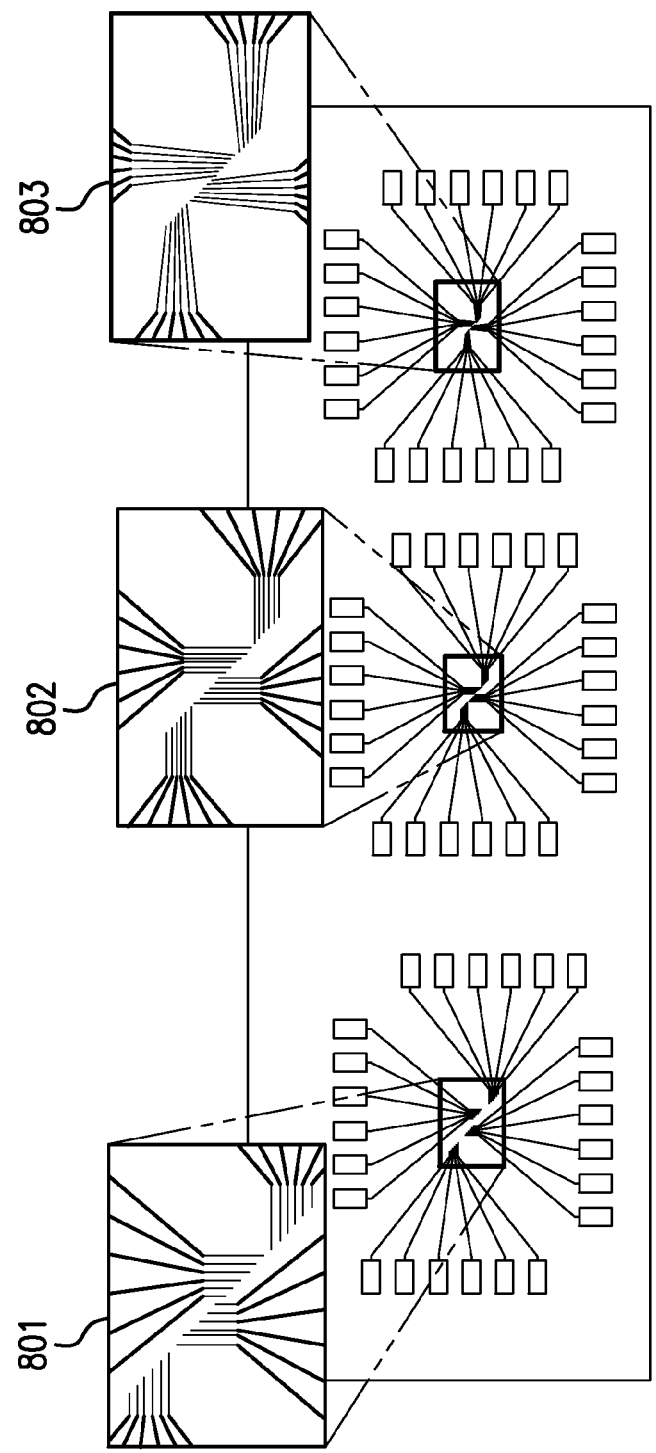
FIG. 8 depicts three exemplary electrode layouts according to an embodiment of the present subject matter.

Additionally, FIG. 8 depicts three exemplary electrode layouts of a microelectrode array according to another embodiment of the present disclosure. In some embodiments, layouts 801, 802, 803 are deposited on a glass slide according to the method described with regard to FIG. 6. The linear configuration of these layouts facilitates studies of conduction velocity of patterned cardiac cells. This geometry enables more physiologically relevant methods for measuring conduction velocity. The cells are aligned and elongated due to boundary conditions imposed by the microprinted geometry. The conduction velocity may be measured by recording cardiac action potential of the cells at multiple points along the linear configuration of the electrodes. With knowledge of the spacing of the electrodes along the linear track, velocity may be determined.

Figure 9A:
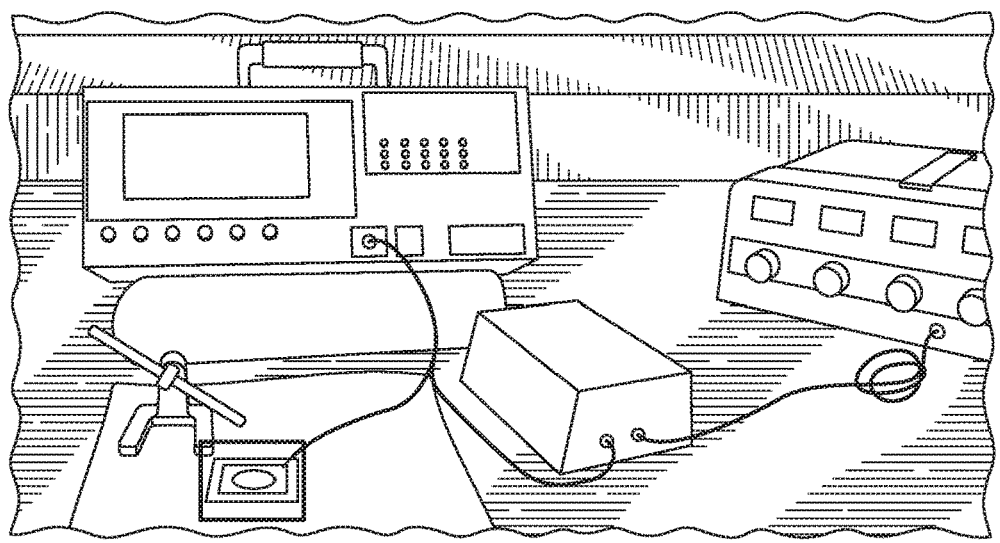
FIGS. 9A-9D depict a system for assessment of cardiotoxicity according to an embodiment of the present subject matter.
Figure 9B:
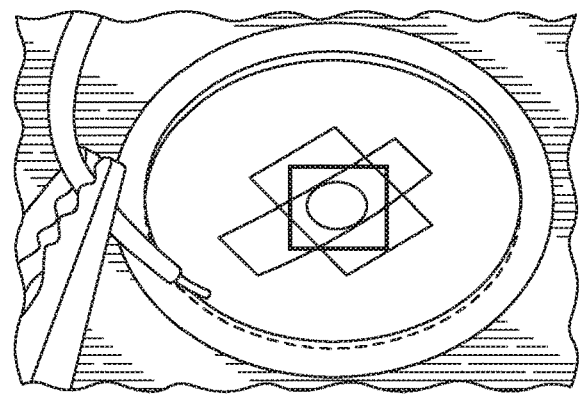
Figure 9C:
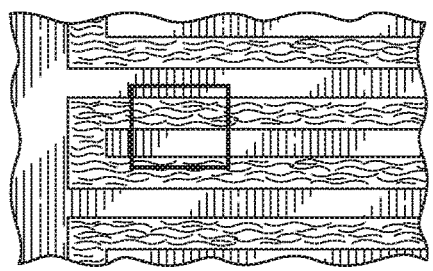
Figure 9D:
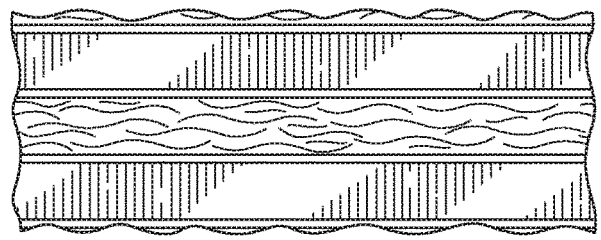

FIGS. 9A-9D depicts a system according to an embodiment of the present disclosure. FIG. 9B shows a microelectrode array in a well format according to an embodiment of the present disclosure. FIG. 9C shows a close-up view of an electrode pattern of the microelectrode array according to an embodiment of the present disclosure. FIG. 9D shows a 10× phase contrast view of neonatal rat cardiomyocytes cultured on micropatterned lines 100 μm in diameter within an electrode pattern according to an embodiment of the present disclosure.

Figure 10:
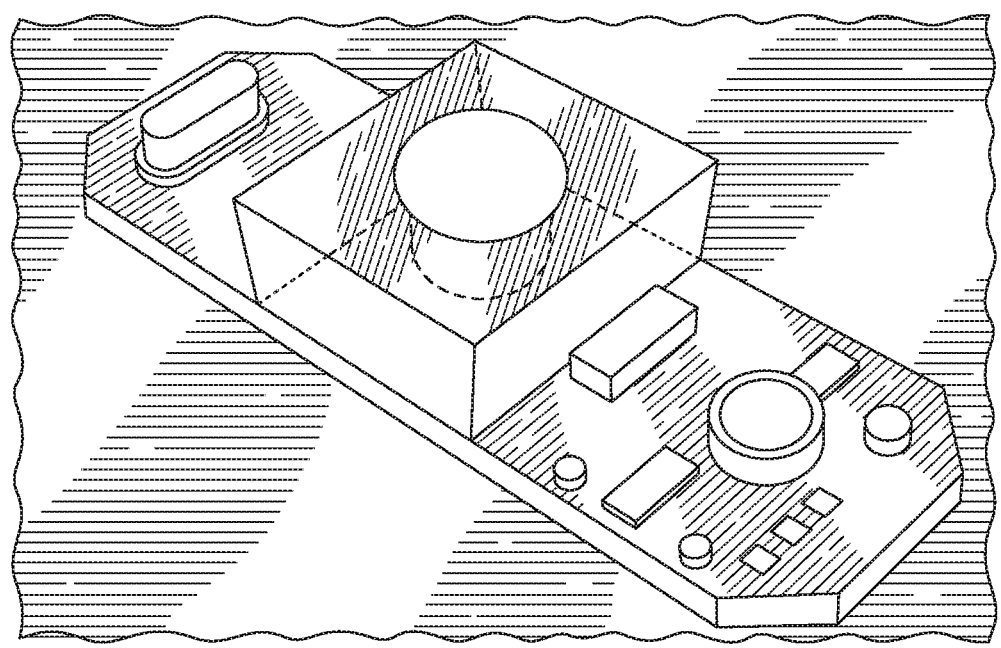
FIG. 10 depicts a culture well according to an embodiment of the present subject matter.

FIG. 10 depicts a culture well integrated with an imaging sensor according to an embodiment of the present disclosure.

Figure 11:
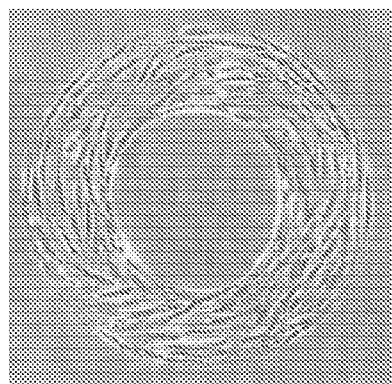
FIG. 11 depicts cardiac cells cultured in a ring pattern according to an embodiment of the present subject matter.

FIG. 11 depicts cardiac cells cultured in a circular pattern.

Figure 12:
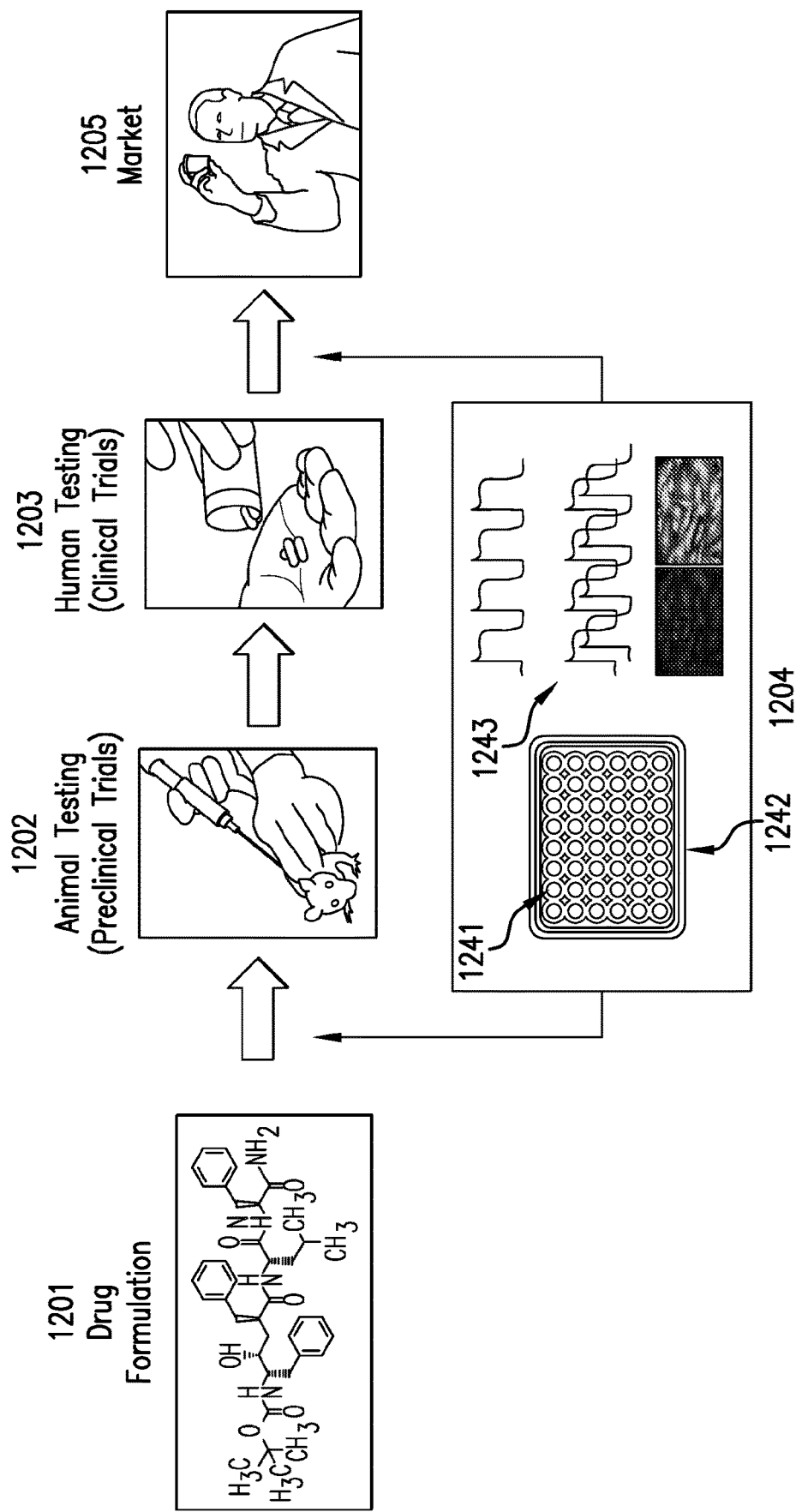
FIG. 12 depicts an exemplary drug screening process according to an embodiment of the present disclosure.

In yet another aspect, a drug screening process is provided, as shown in FIG. 12. Screening 1204 can be performed with a microelectrode array in accordance with the embodiments described herein as early as before preclinical animal testing 1202. If desired, drug screening can take place before market 1205. In an exemplary embodiment, screening 1204 is performed using a kit 1242 including a plurality of microelectrode arrays (e.g., 1241). The microelectrode arrays of kit 1242 can have a variety of different layouts or patterns, and a variety of different cell culture patterns. The output signals 1243 of the various microelectrode arrays are recorded and analyzed to determine whether a drug introduced to the cell cultures have any undesirable cardiac or efficacy effects. In this manner, screening can detect drug failures earlier in the drug development plan saving companies from expending extraordinary costs in drug development.

Figure 13:
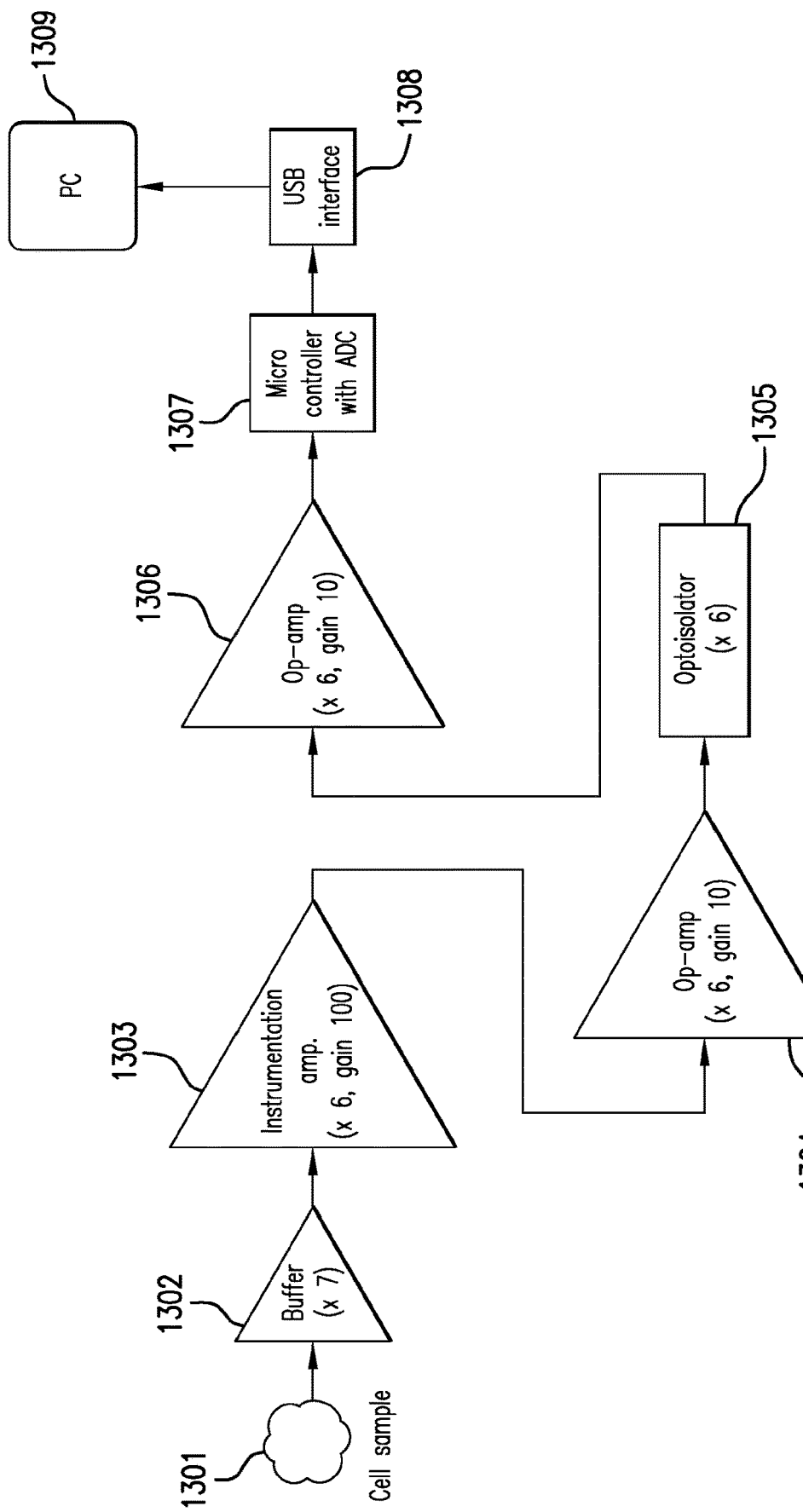
FIG. 13 is a schematic view of an amplifier design according to an embodiment of the present disclosure.
Figure 14A:
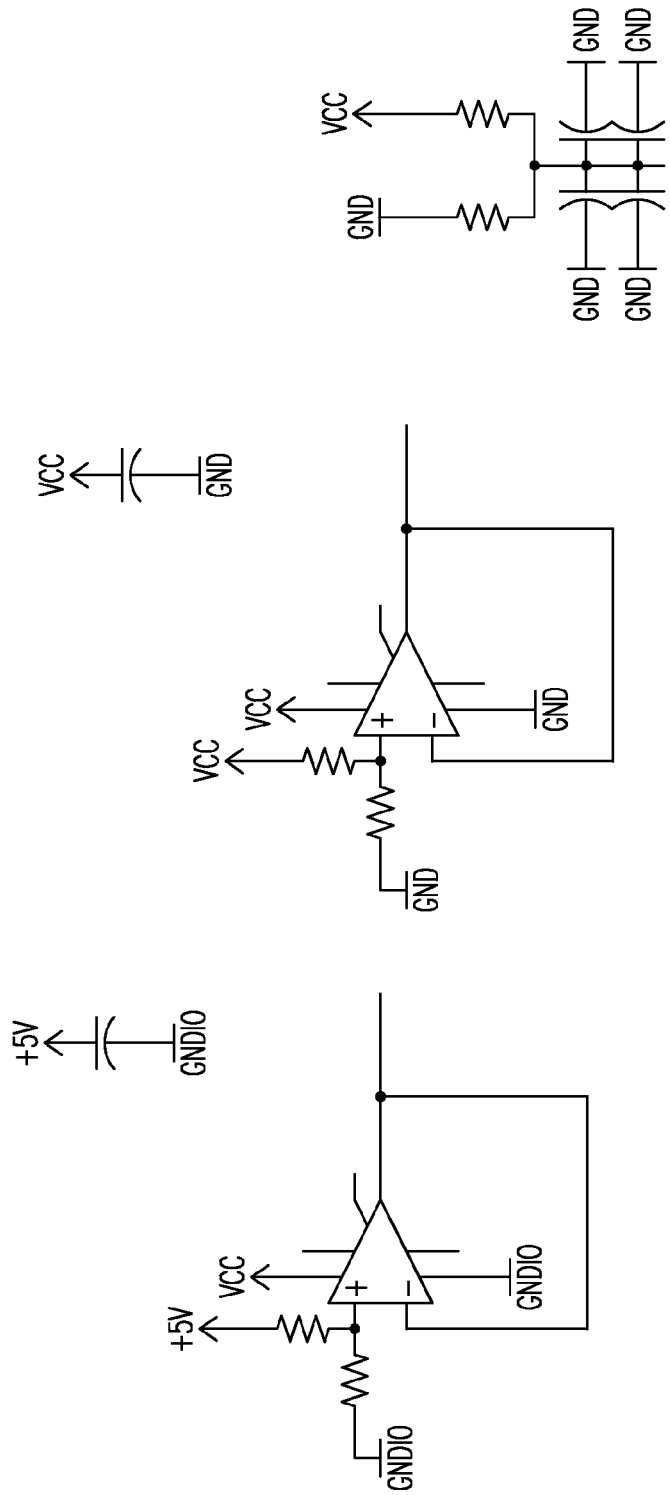
FIGS. 14A-14O are schematic representations of circuit diagrams of an amplifier according to an exemplary embodiment of the present subject matter.
Figure 14B:
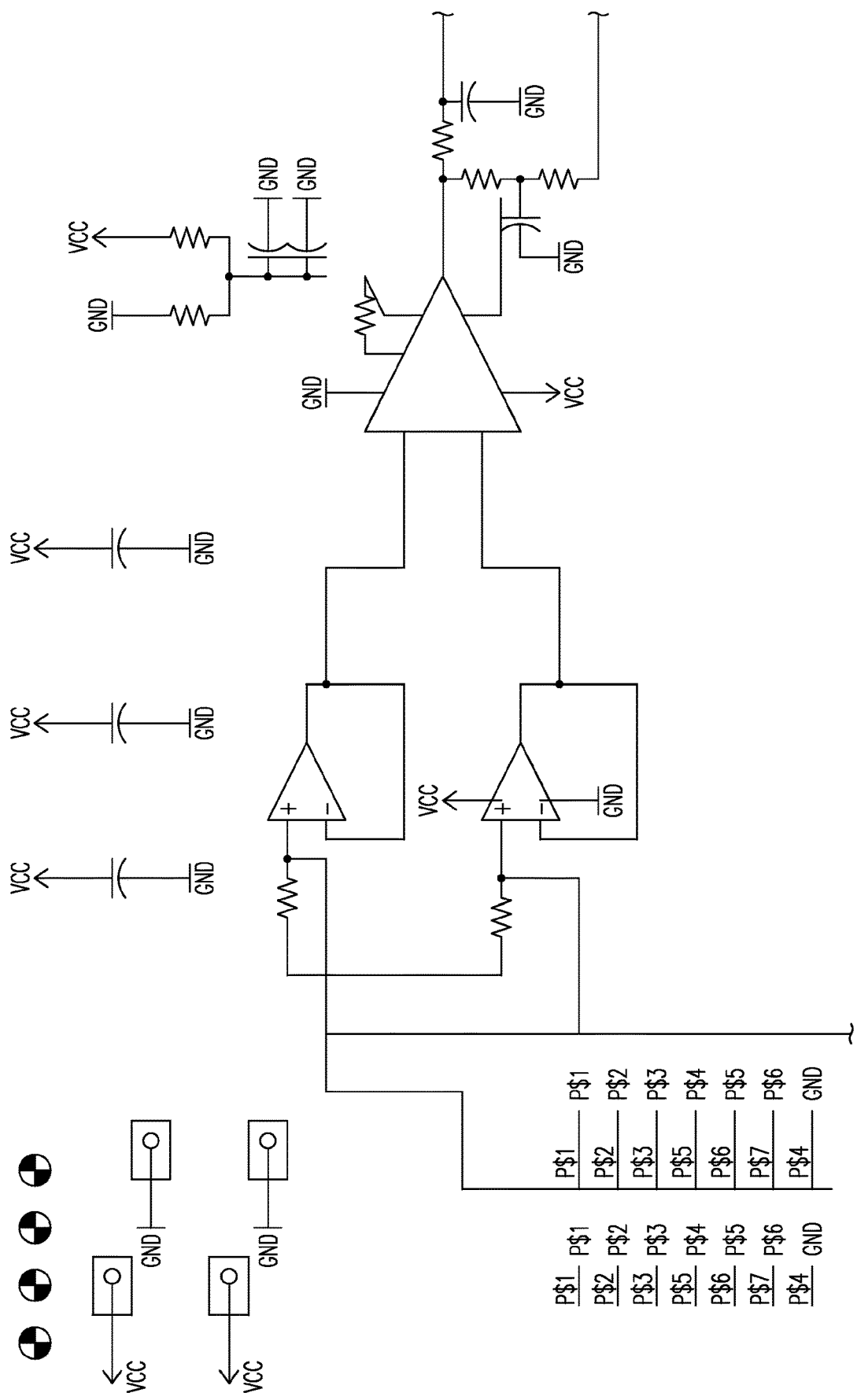
Figure 14C:
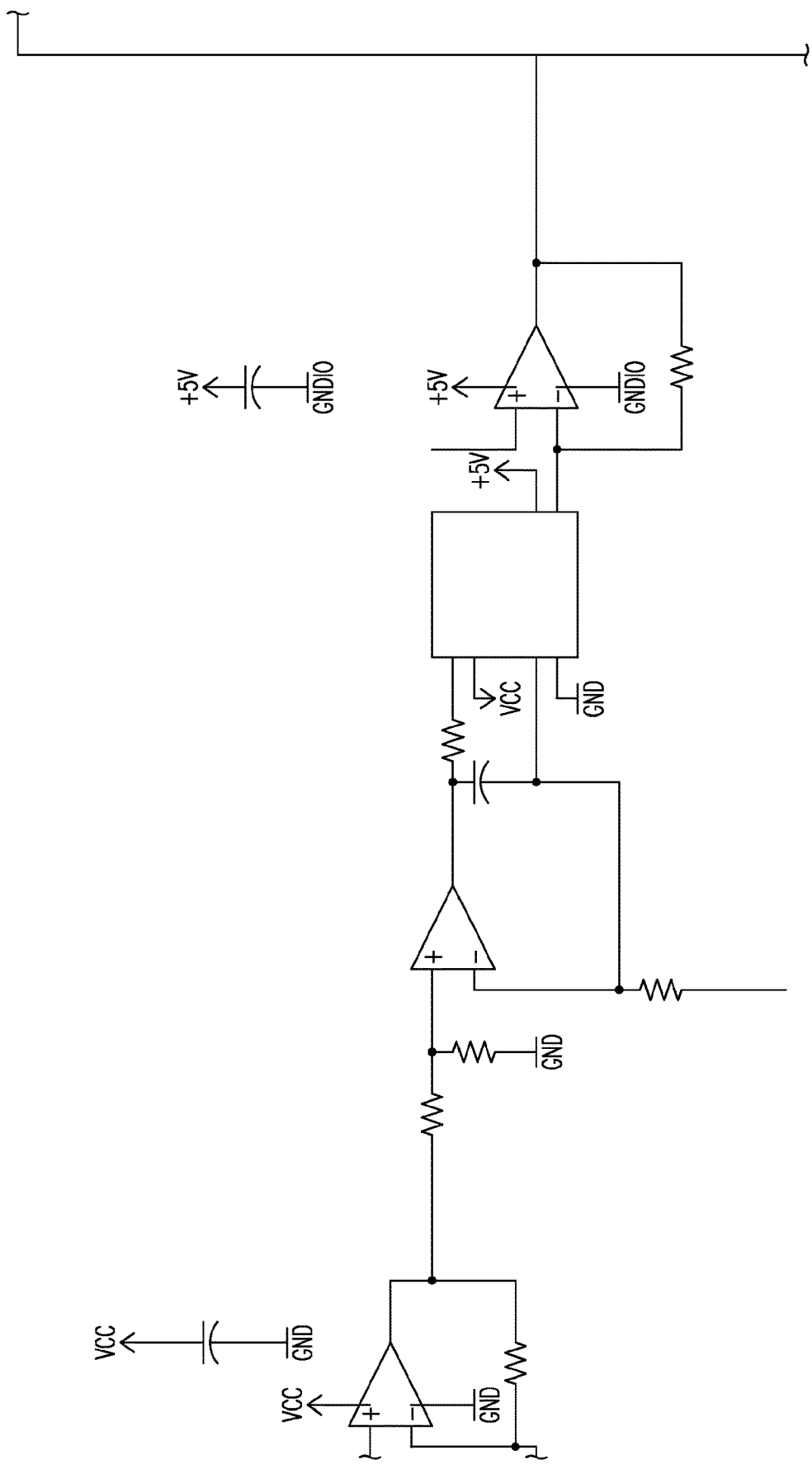
Figure 14D:
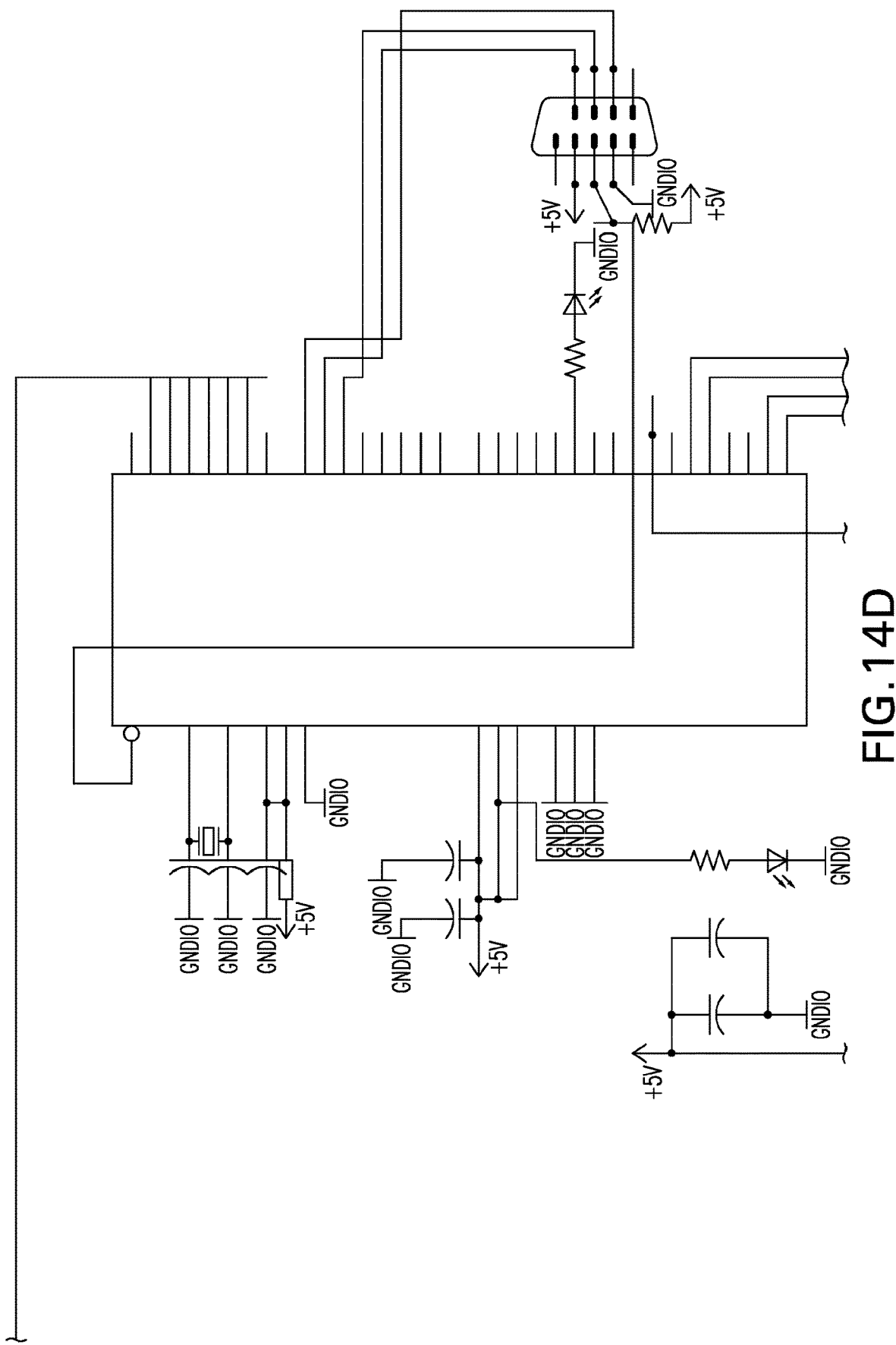
Figure 14E:
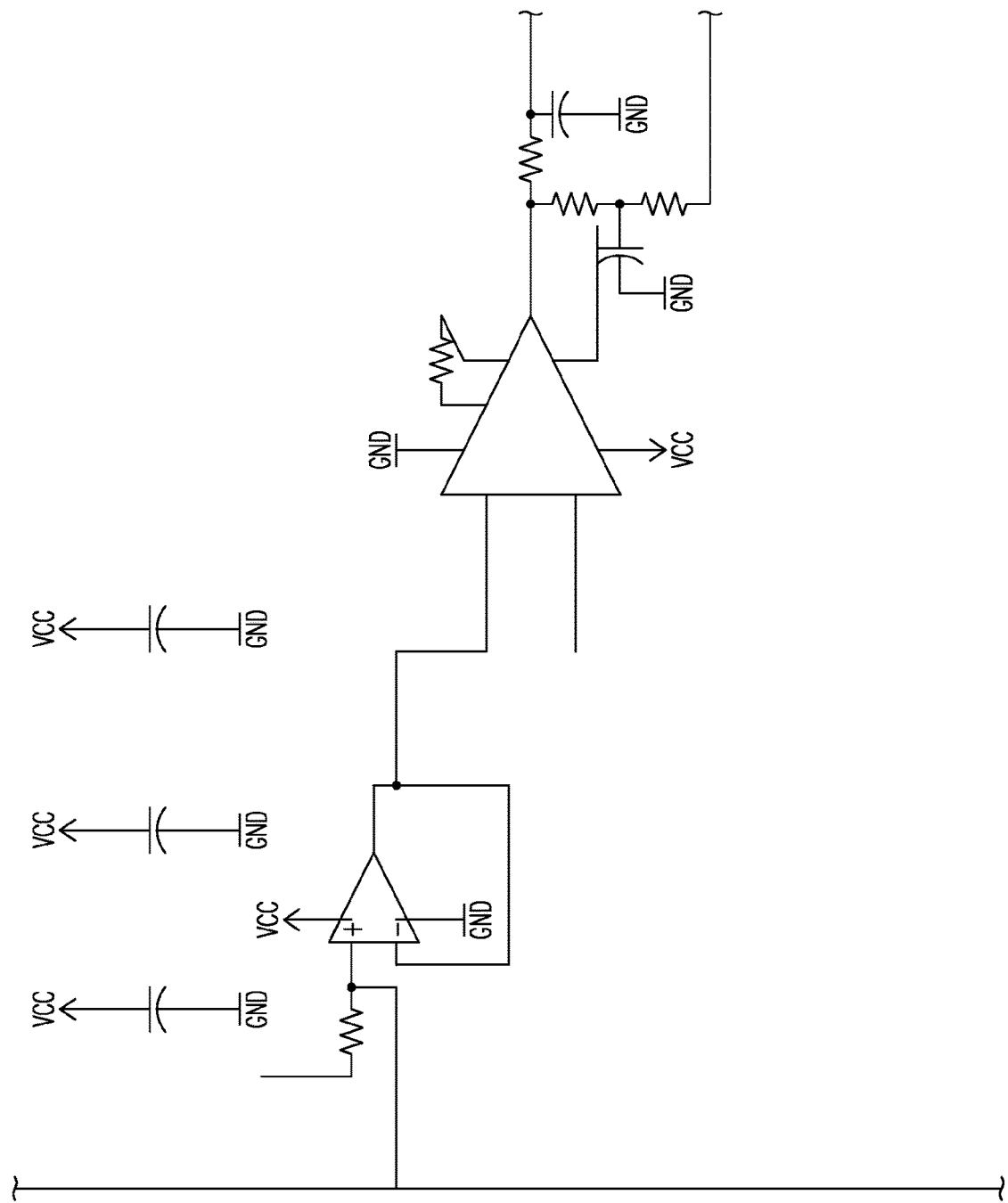
Figure 14F:
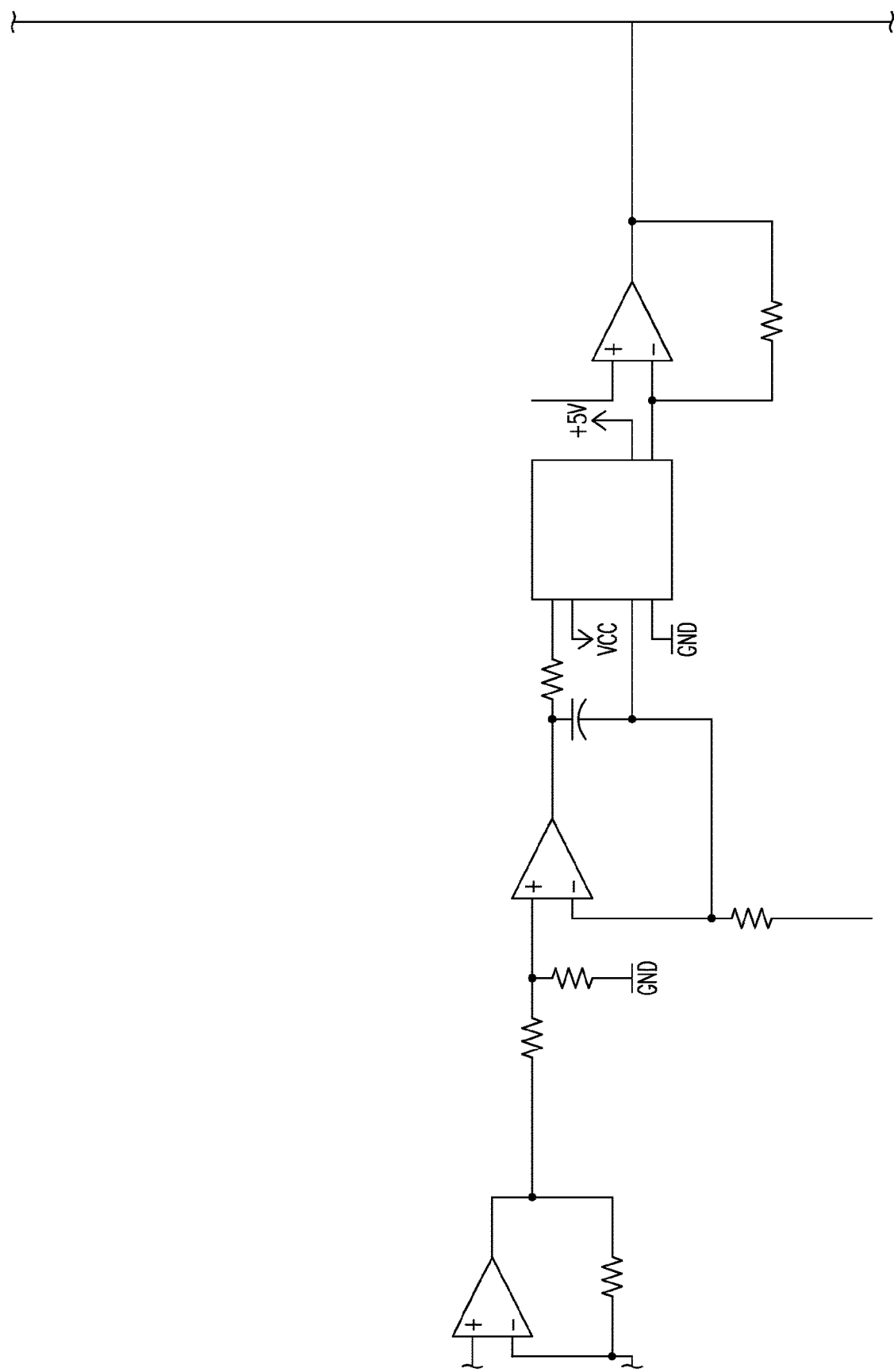
Figure 14G:
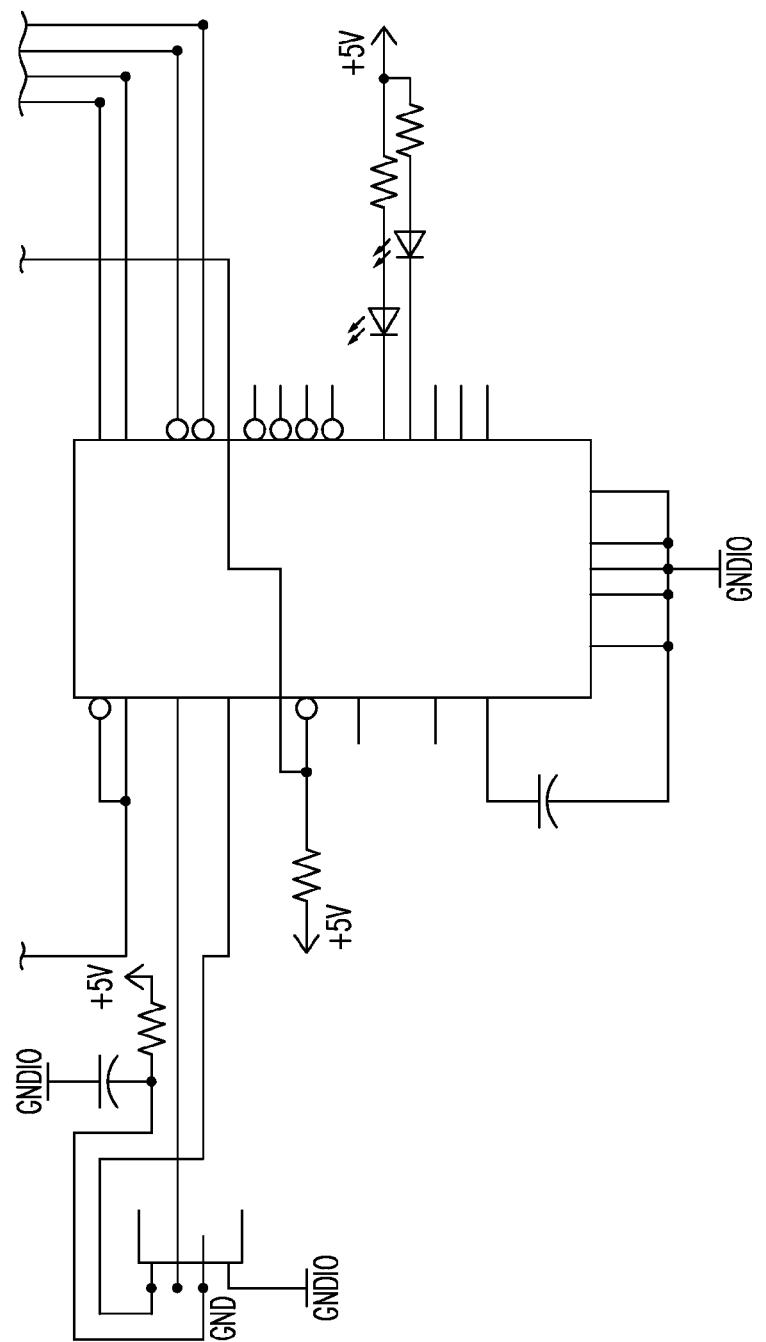
Figure 14H:
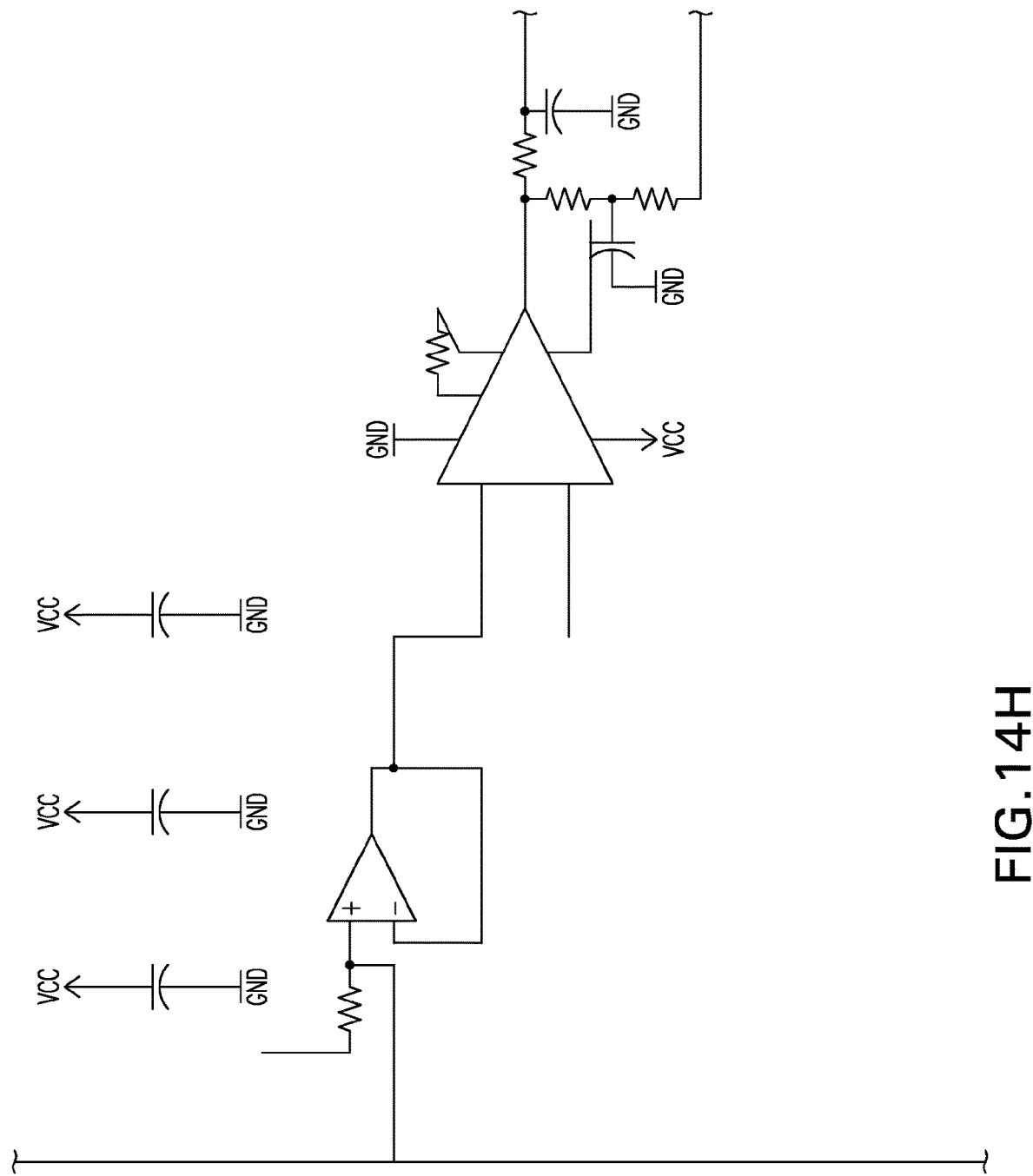
Figure 14I:
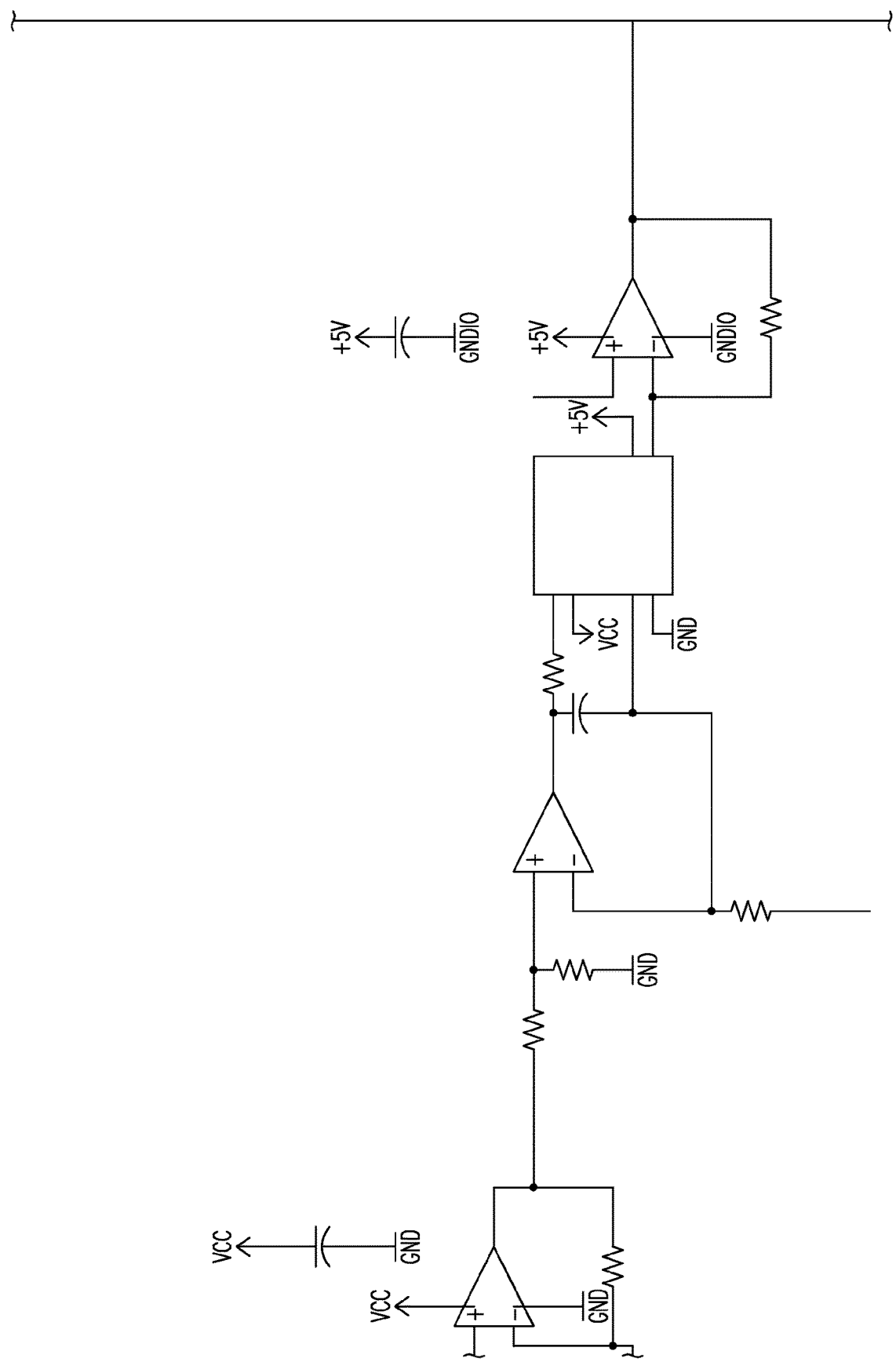
Figure 14J:
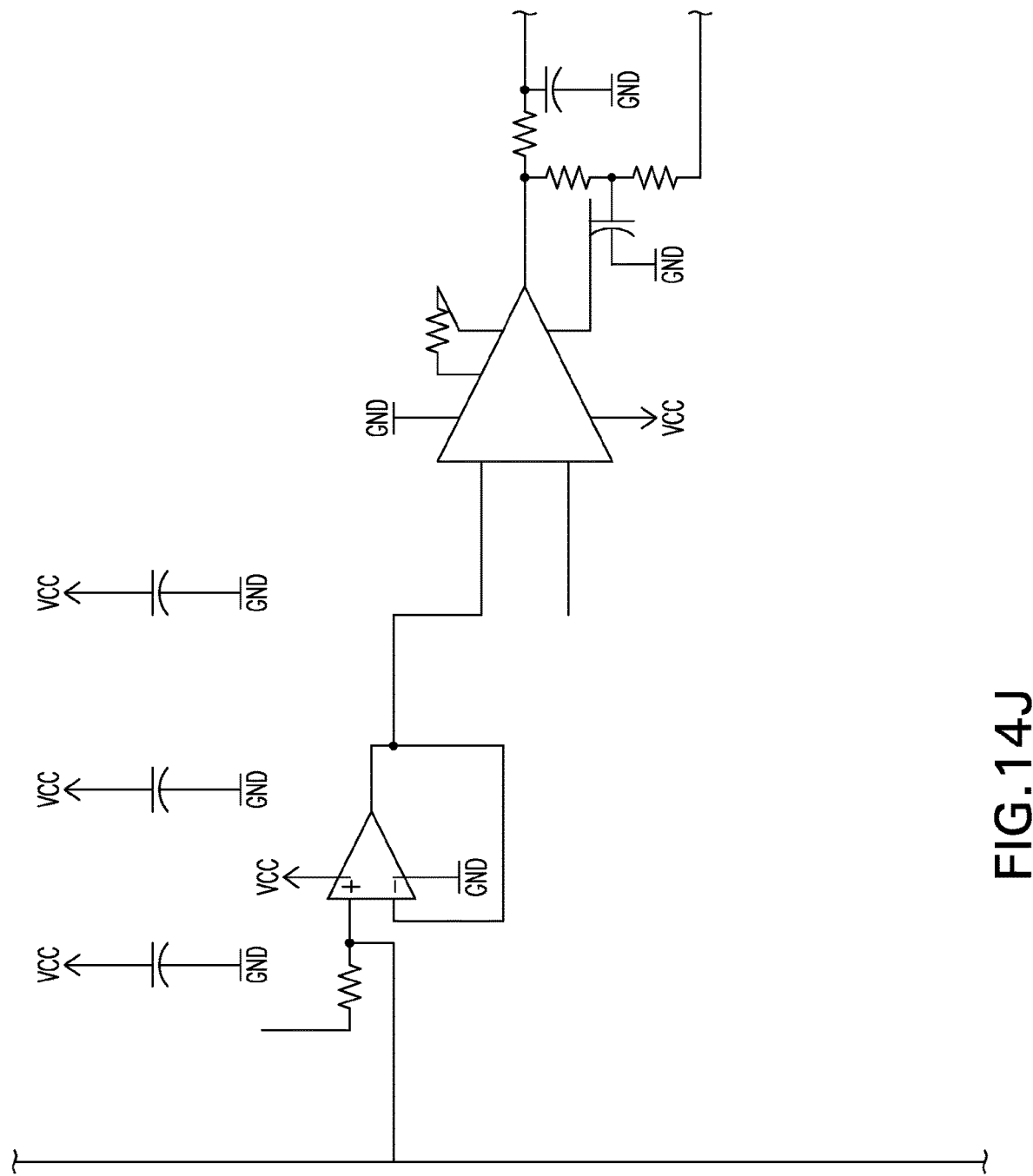
Figure 14K:
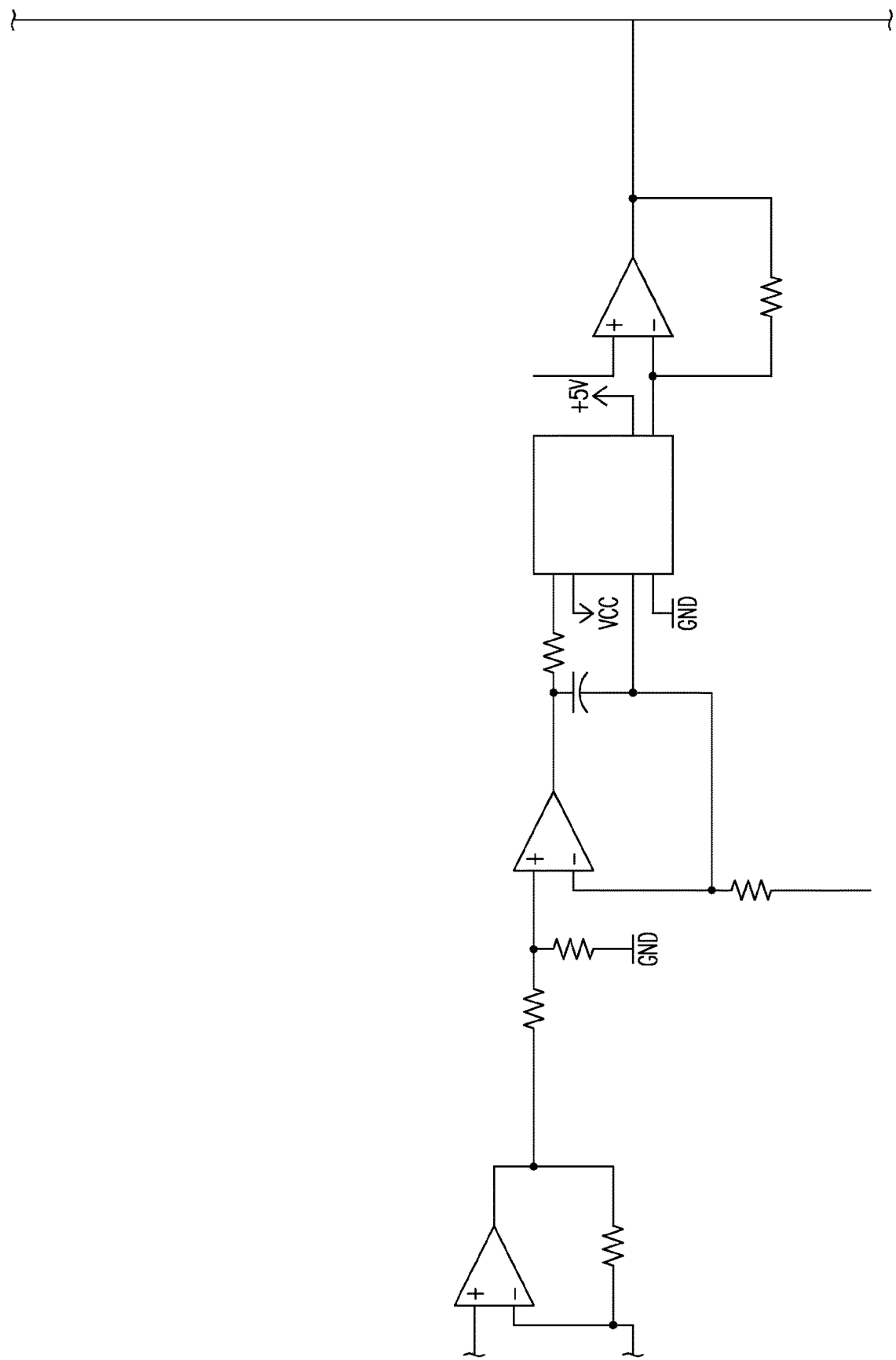
Figure 14L:
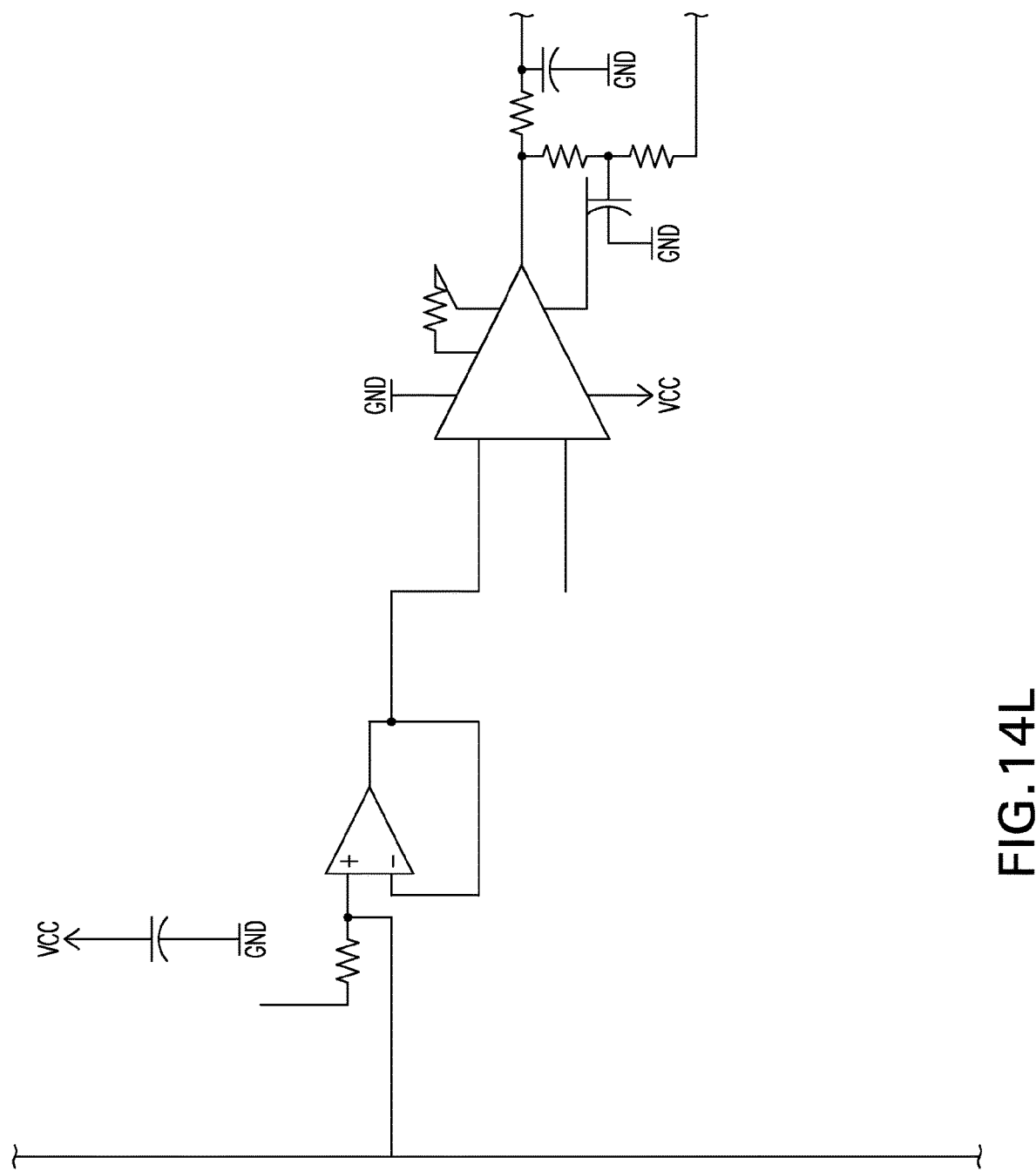
Figure 14M:
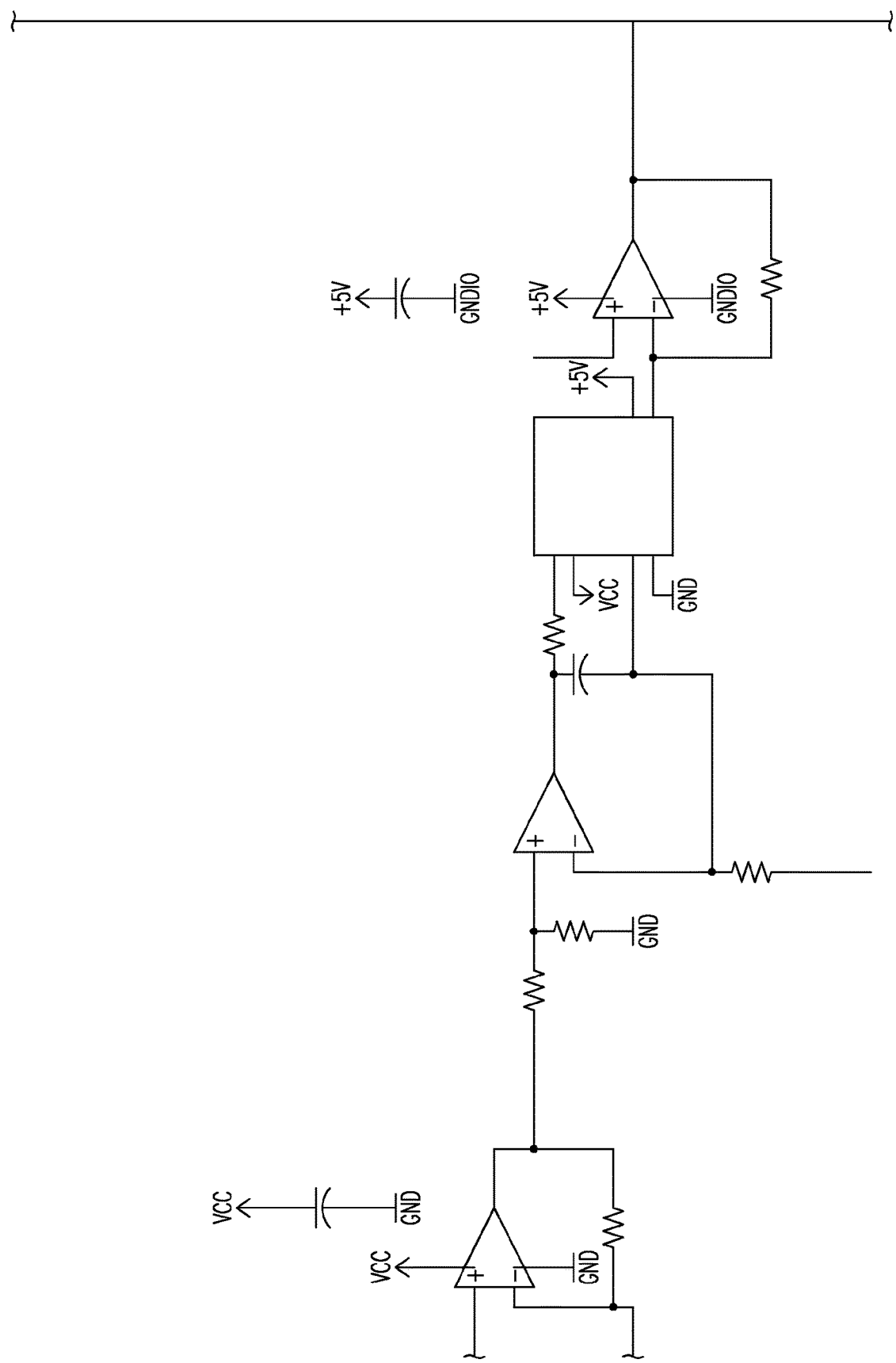
Figure 14N:
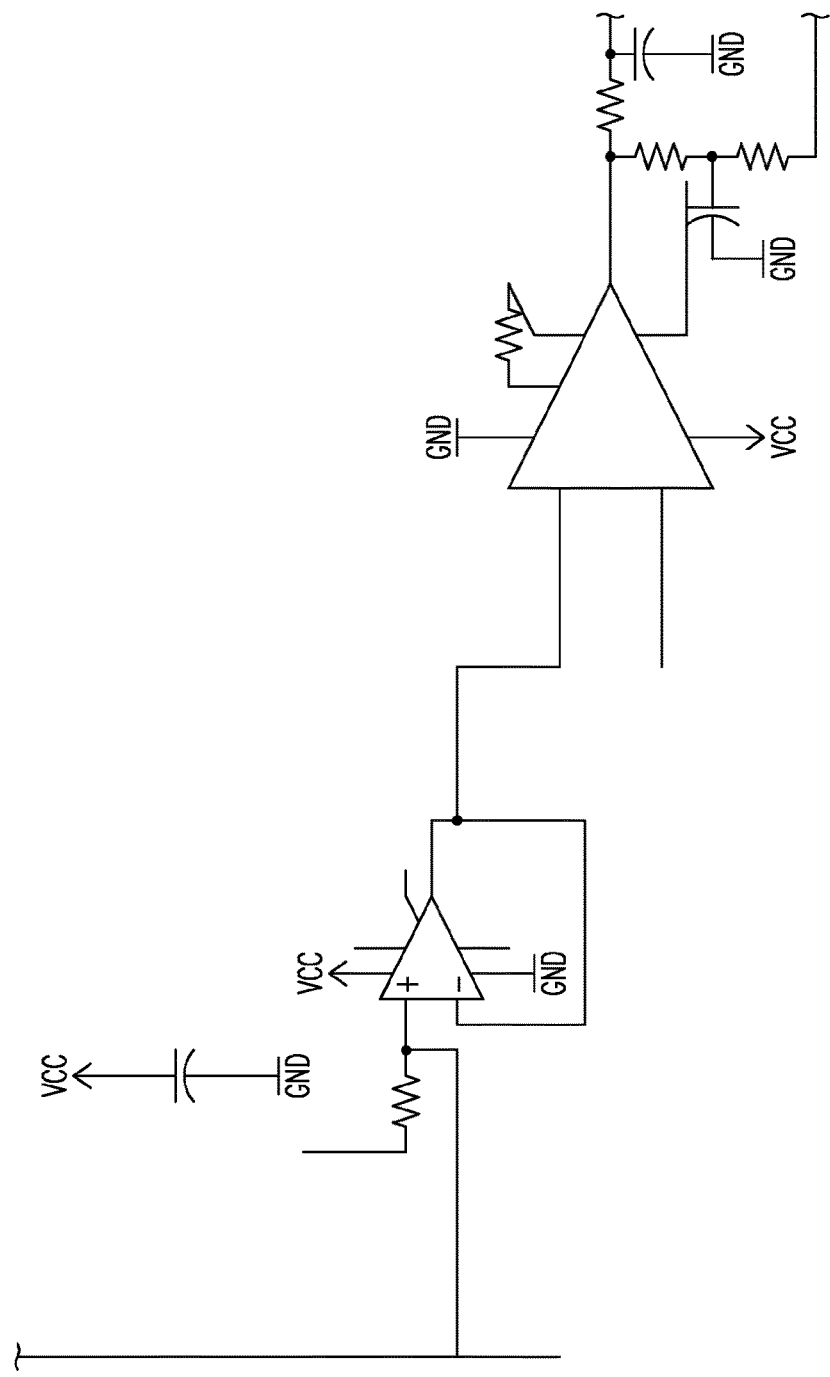
Figure 14O:
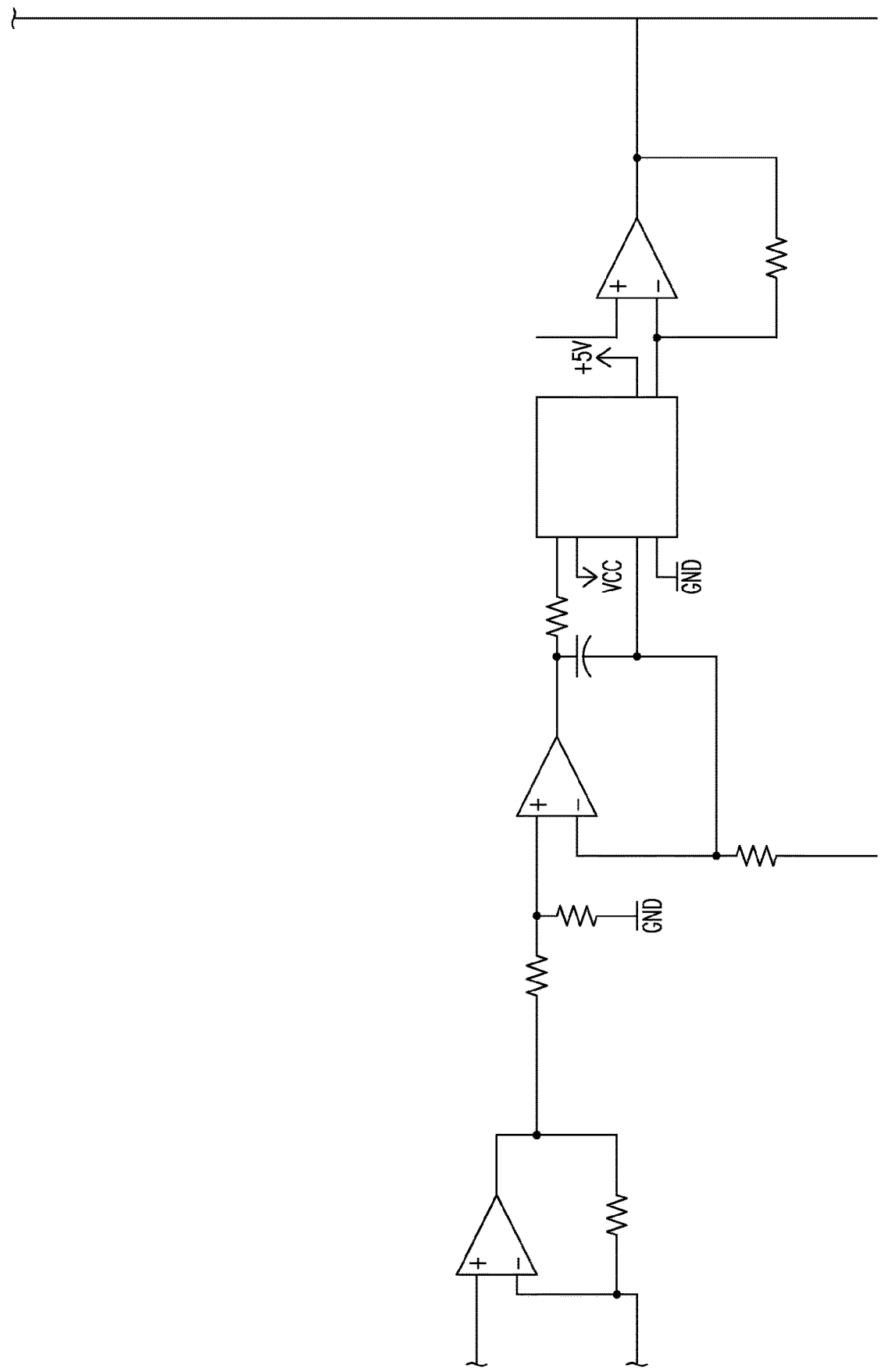

FIG. 13 depicts a schematic view of an amplifier design according to an embodiment of the present disclosure. The design reduces signal noise, and isolates signal acquisition from transmission and processing. Signals from cell sample 1301 feed into seven buffer circuits 1302. Six of the buffer circuits 1302 correspond to one electrode in the microelectrode array. The seventh of the buffer circuits 1302 corresponds to ground. The output of each of the six electrode buffer circuits 1302 are fed through an instrumentation amplifier stage 1303 followed by an operational amplifier stage 1304. In some embodiments, the instrumentation amplifier stage 1303 has a voltage gain of 100 and the operational amplifier stage 1304 has a voltage gain of 10. The output of operational amplifier stage 1304 feeds into optoisolator stage 1305. Optoisolator stage 1305 is operable for shielding high-noise circuitry for data transfer from circuitry interfacing with cells. The output of the optoisolator 1305 feeds into operational amplifier stage 1306. In some embodiments, the operational amplifier stage 1306 has a voltage gain of 10. The output of operational amplifier stage 1306 feeds into micro-controller 1307, which comprises an analog-to-digital converter. Micro-controller 1307 provides output via USB interface 1308 to PC 1309.

FIG. 14 provides a circuit diagram of an amplifier according to an embodiment of the present disclosure.

Figure 15A:
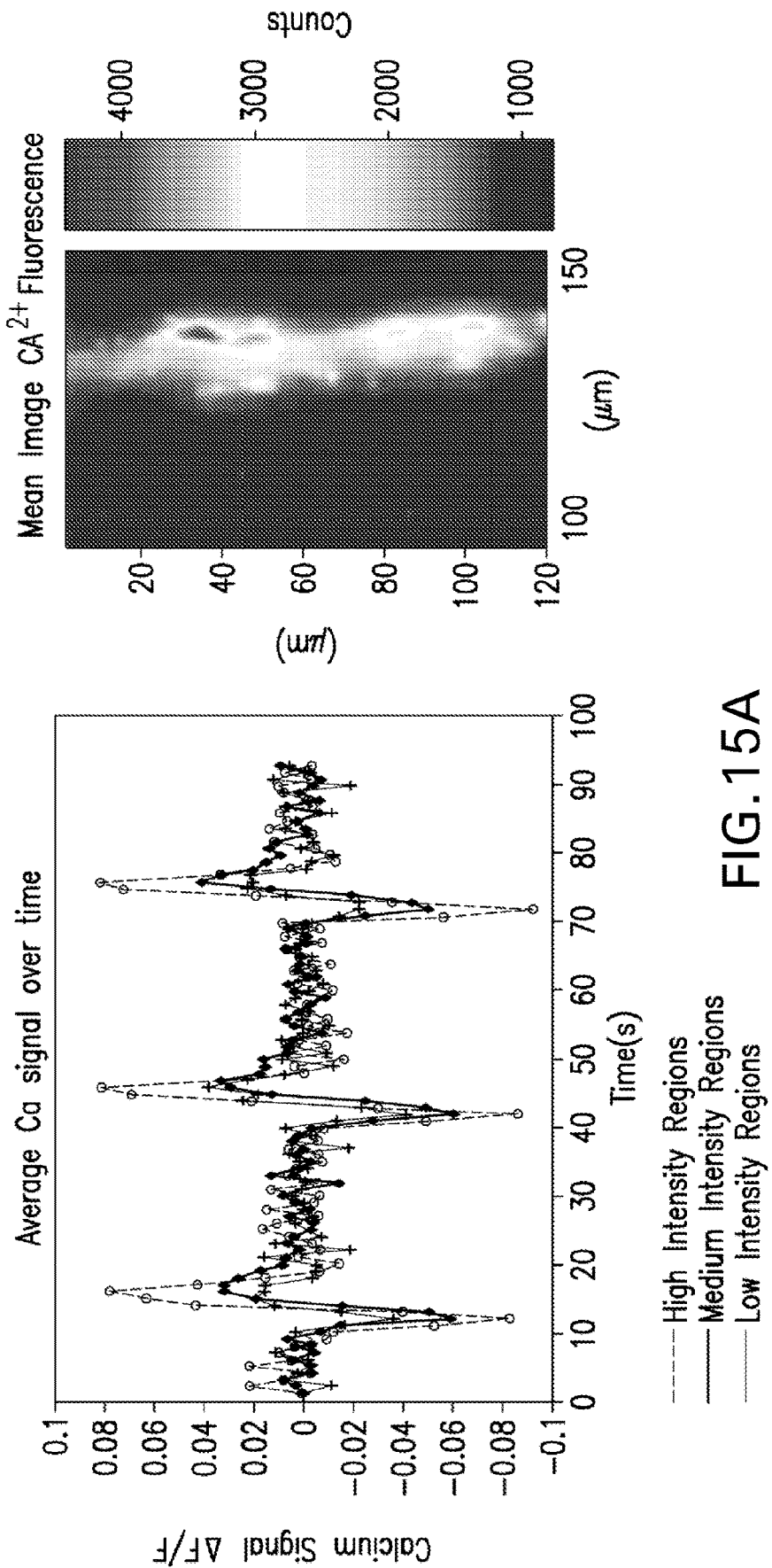
FIGS. 15A-15B are sample outputs according to an exemplary embodiments of the present disclosure.
Figure 15B:
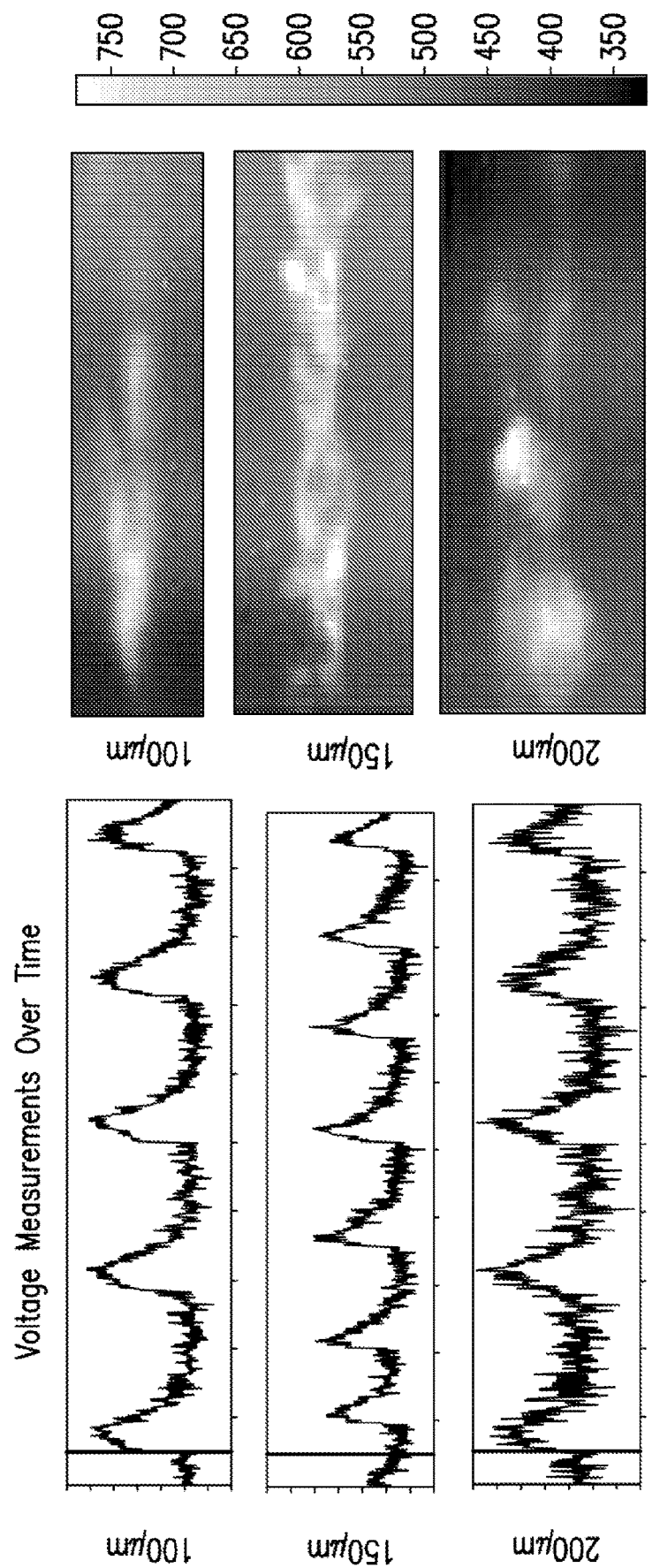

As discussed above, in embodiments of the present disclosure, the cell culture occurs over a transparent microelectrode plate 202, with the cell culture well defined by a PDMS mold 203. The growth platform is therefore transparent. An optically transparent platform allows for simultaneous electrical and optical data acquisition using microelectrodes 221 and imaging sensor 201. In some embodiments, electrical and calcium signals are measured simultaneously. The optically transparent platform allow for image analysis of a cell's contracting and/or cellular fluxes due to the tracking of fluorescent calcium or voltage dyes. This directly translates into a more precise spectral analysis that is more reflective of the state of the tissue at that time. Sample output is shown in FIG. 15.

According to an aspect of the present disclosure, custom MEA fabrication enables control of the patterns of cells and the respective patterned electrodes. Micropatterning of both cells and electrodes allows well-controlled studies of geometrical and spatial interactions between the cells, while simultaneously tracking electrical propagation along distinct paths. Micropatterning also allows for uniform production of high numbers of tissue/electrode systems, reducing variability between samples, and facilitating screening studies. Production of uniform cardiac tissues reduces the need for animal experimentation and allows for the examination of detailed intracellular mechanisms. Patterning cells controls cell alignment and elongation to enable physiologically relevant spatiotemporal tracking. Patterned cells align and elongate due to the imposition of geometric boundaries. In some embodiments, a protein is provided in the cell growth region. This protein may provide suitable growth medium and cellular adhesion properties. In some embodiments, the protein is fibronectin.

Figure 16A:
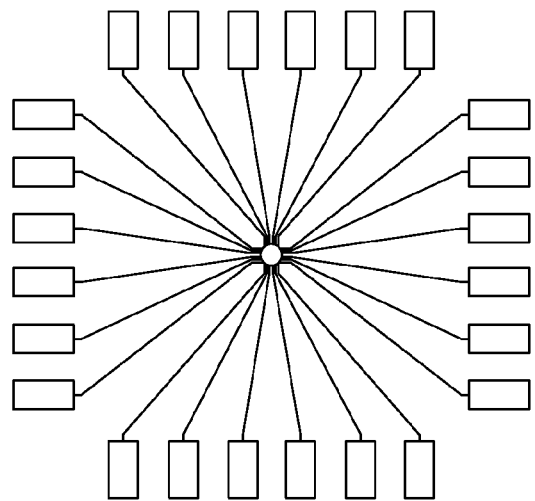
FIGS. 16A-B show an exemplary ring configuration of micropatterned electrodes according to an embodiment of the present disclosure.
Figure 16B:
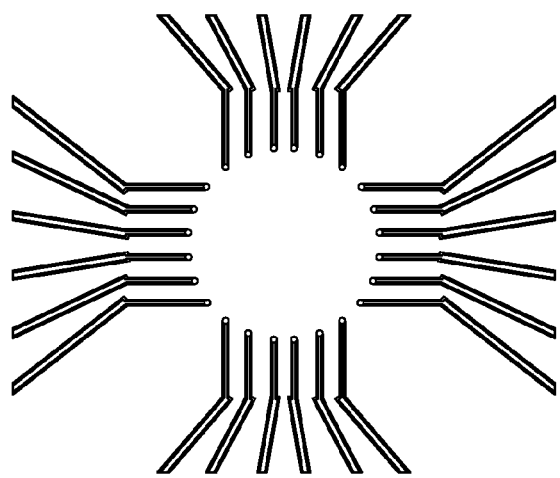
Figure 17:
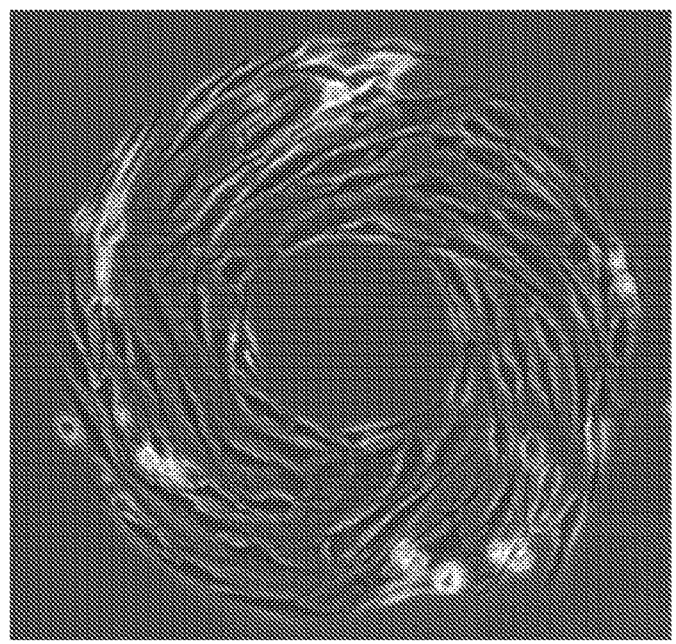
FIG. 17 depicts micropatterned stem cells according to an embodiment of the present disclosure.

FIG. 16A shows an exemplary ring configuration of micropatterned electrodes, with FIG. 16B showing an enlarged view of the central ring region of FIG. 16A. FIG. 17 depicts micropatterned stem cells in the corresponding ring configuration.

Figure 18A:
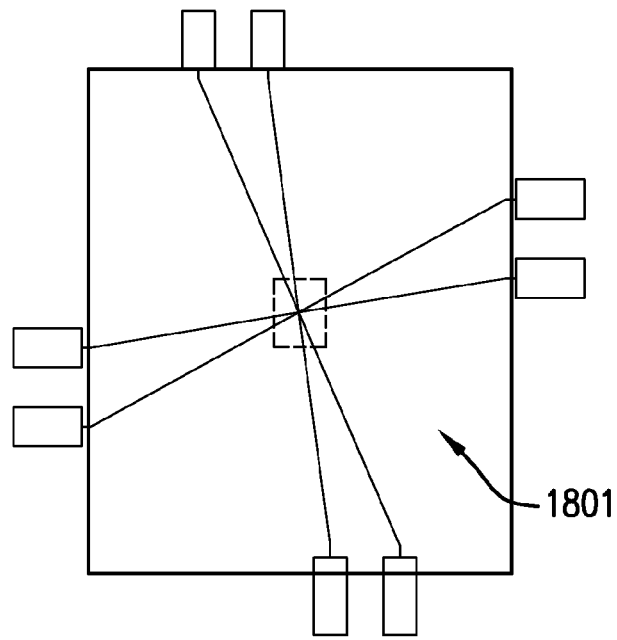
FIGS. 18A-B depicts an exemplary ring configuration of micropatterned electrodes according to an embodiment of the present disclosure.
Figure 18B:
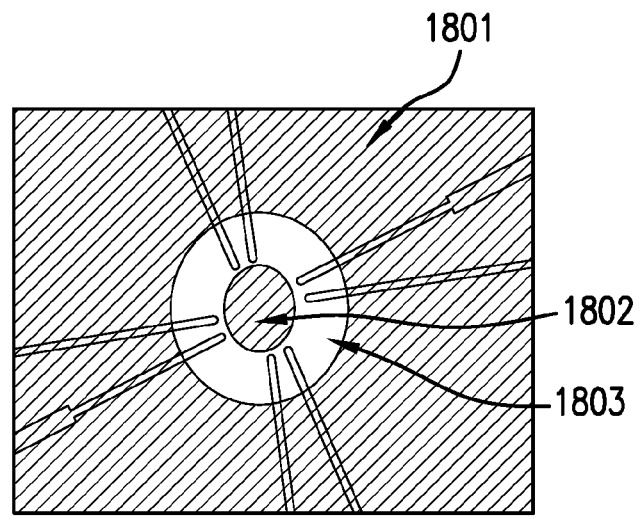

FIG. 18A shows a second exemplary ring configuration of micropatterned electrodes with FIG. 18B showing an enlarged view of the central ring region of FIG. 18A. Controlled patterning of $SiO_2$ glass areas 1801, 1802 allows the inherent incorporation of regions for microcontact printing. By chemically modifying the surfaces where the glass is not patterned versus areas where the glass is patterned, preferential cell attachment areas may be controlled. Height difference enables facile chemical modification—a PDMS stamp coated with intended chemical can just be "stamped" onto the microelectrode array (MEA). Uncovered portion 1803 allows contact with the underlying electrodes. This this configuration, uncovered portion 1803 forms an annulus. Annular arrangements according to embodiments of the present disclosure are suitable for measurement of conduction velocity over time. In particular, with knowledge of the spacing of the electrodes within the annular cell-bearing region, velocity may be determined from the detected action potential of the cells. By virtue of the ring arrangement, the change in velocity over time may be determined.

Figure 19A:
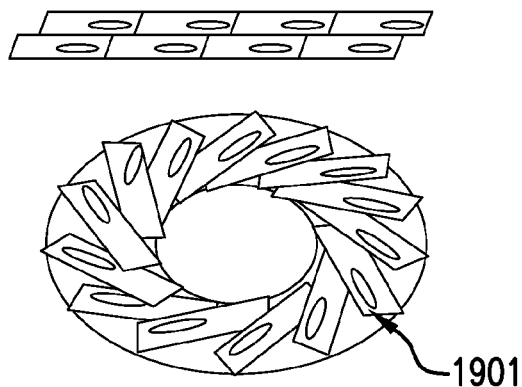
FIGS. 19A-C depict exemplary microelectrode array designs for cardiac disease modeling according to an embodiment of the present disclosure.
Figure 19B:
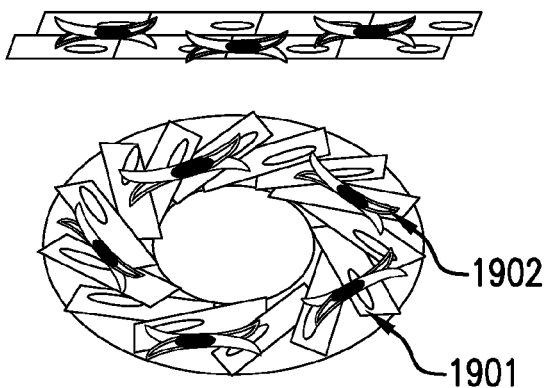
Figure 19C:
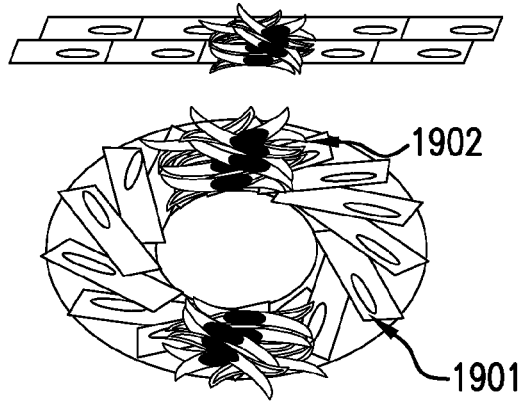

FIGS. 19A-19C depicts exemplary microelectrode array designs for cardiac disease modeling. Myocardial tissue relies on the complex organization of cardiac muscle cells (CMs) and matrix-producing fibroblasts (FBs) for proper electrical and mechanical heart properties. Cardiac Disease is characterized by infarct regions with increased amounts of scar tissue (produced by fibroblasts) that lead to "conduction blocks" in diseased tissue. Cell patterning allows for precise positioning of CMs and FBs to perform controllable studies of cardiac disease. FIG. 19A depicts an exemplary ring arrangement of cardiac muscle cells 1901. FIG. 19B depicts an exemplary ring arrangement of cardiac muscle cells 1901 with differing percentages of fibroblasts 1902. FIG. 19C depicts an exemplary ring arrangement of cardiac muscle cells 1901 with conduction blocks of fibroblasts 1902.

Figure 20A:
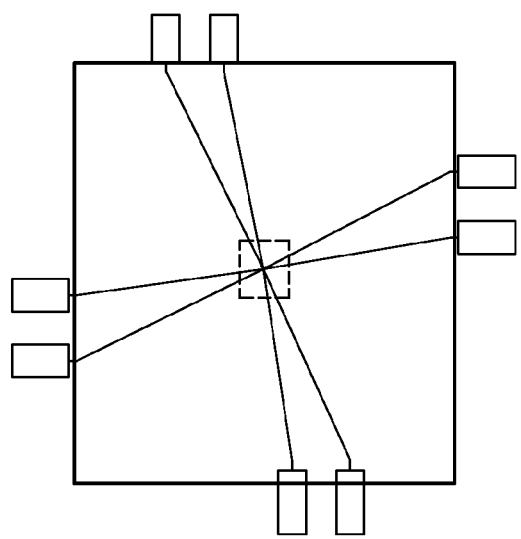
FIGS. 20A-B show an exemplary configuration of micropatterned electrodes suitable for use in an arrhythmia model according to an embodiment of the present disclosure.
Figure 20B:
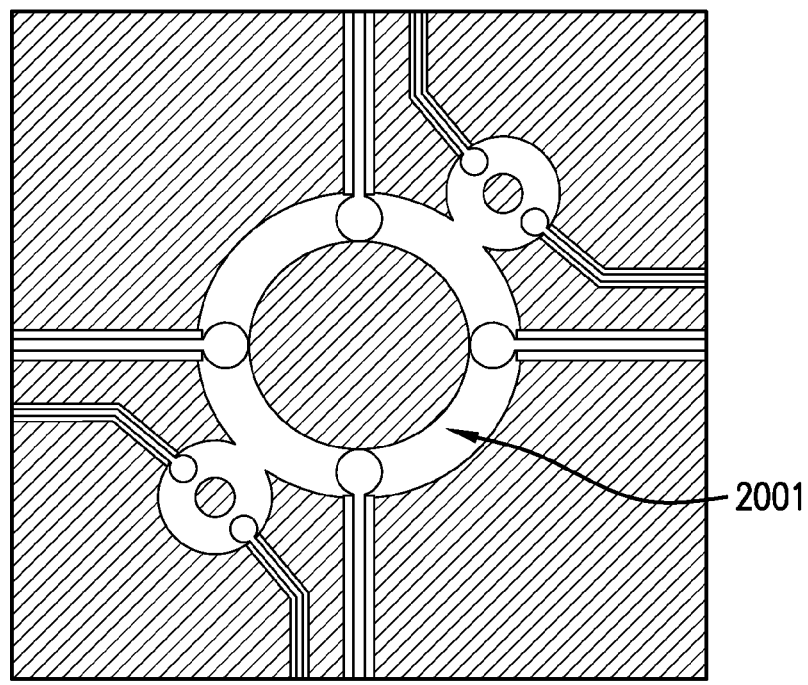

FIG. 20A shows an exemplary configuration of micropatterned electrodes suitable for use in an arrhythmia model, with FIG. 20B showing an enlarged view of the central region of FIG. 20A. The multiple ring configuration of FIG. 20 enables modeling of reentrant spiral waves. Reentrant spiral waves are the leading cause of tachyarrhythmias. Models for reentrant arrhythmia are mostly in silico (i.e. computer simulations). Cell-patterned reentrant loops according to an embodiment of the present disclosure allow systematic in vitro studies of arrhythmia. In this configuration, uncovered portion 2001 forms three overlapping annuli. In other embodiments, other numbers of overlapping annuli are provided. In some embodiments, the smaller annuli are sized such that the cardiac action potentials of the cultured cells propagate along the circumference of each annulus in a time greater than the refractory period of the cells.

In addition to the embodiments discussed above, the present subject matter is applicable to various fields of biological research. In particular, embodiments of the present disclosure are useful for electrophysiology research, cardiac developmental biology research, and cardiac tissue engineering, as well as evaluation of cardiotoxicity.

Figure 21A:
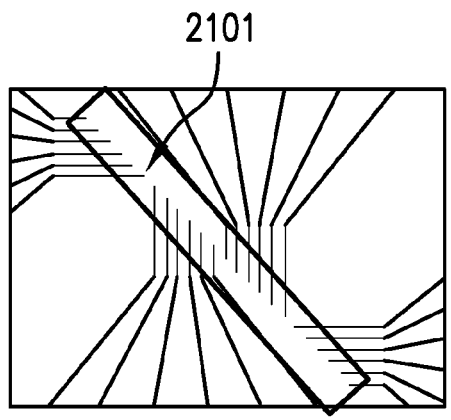
FIGS. 21A-C show exemplary configurations of micropatterned electrodes suitable for use in measuring conduction velocity of cells.
Figure 21B:
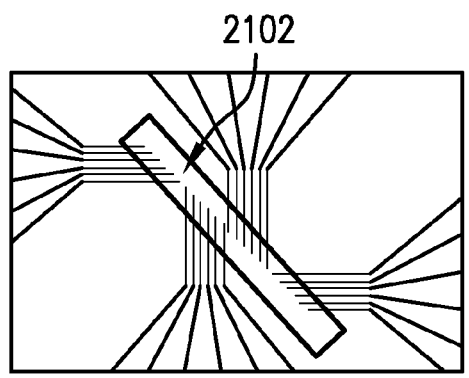
Figure 21C:
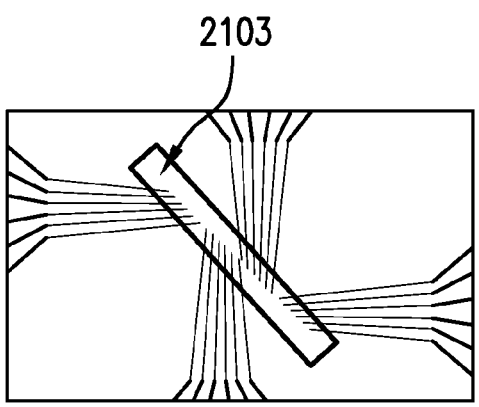

FIGS. 21A-B depict exemplary linear configurations of micropatterned electrodes. Uncovered regions 2101, 2102, 2103 form stripes suitable for deposition of cells under study. In some embodiments, uncovered regions 2101, 2102, 2103 are substantially rectangular, with widths from 50 μm to 300 μm. In some embodiments, the ration of the length to the width of the stripe is from three to ten. In some embodiments, multiple rectangular stripes are provided on one substrate.

Figure 22A:
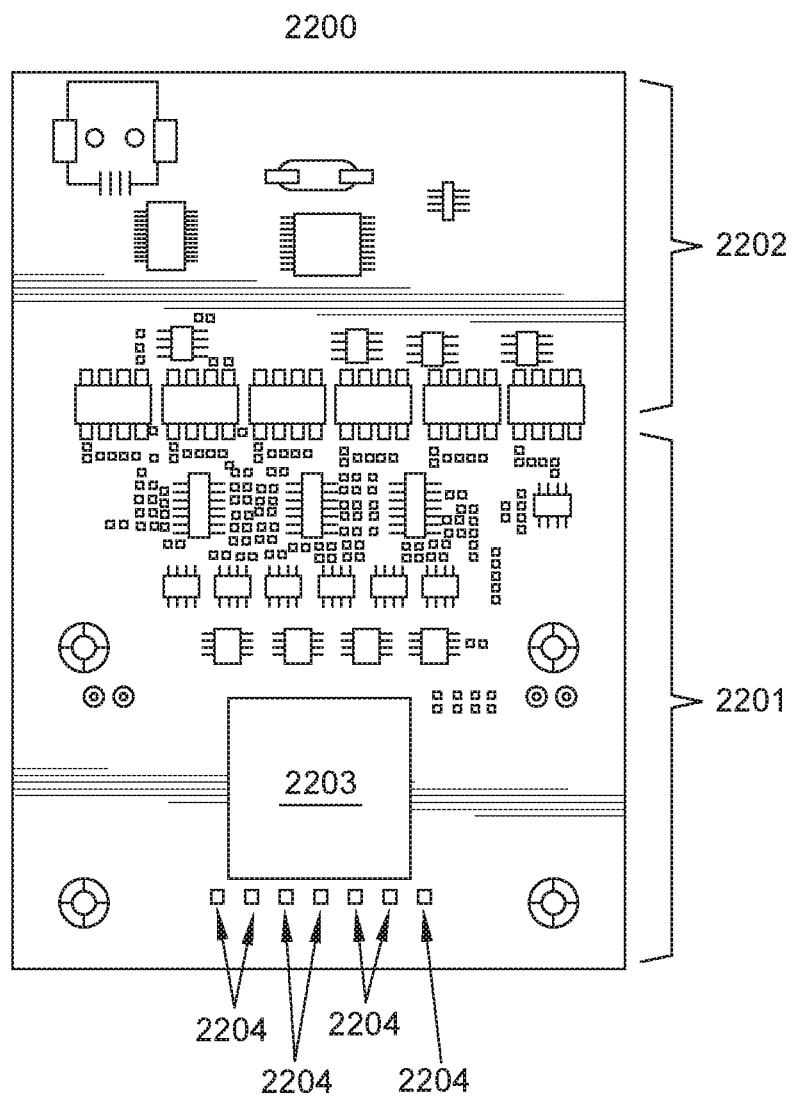
FIG. 22A-C show an exemplary physical configuration of a device according to an embodiment of the present disclosure.
Figure 22B:
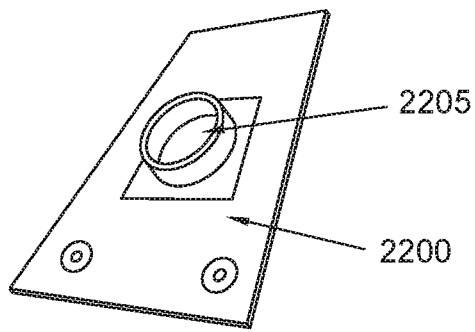
Figure 22C:
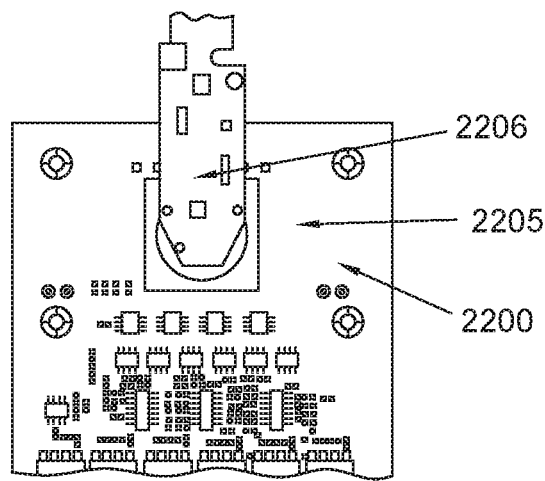

FIG. 22A depicts an exemplary physical layout of a device according to an embodiment of the present disclosure. Main PCB 2200 comprises MEA interface portion 2201 and external interface portion 2202. MEA interface portion 2201 is electrically isolated from external interface portion 2202 by a plurality of opto-isolators (not pictured). MEA interface portion 2201 comprises a void 2203 for penetration of an MEA assembly. MEA interface portion 2201 further comprises a plurality of contacts 2204 for electrically connecting with an MEA assembly. In some embodiments, MEA interface portion 2201 is powered by battery while external interface portion 2202 is powered via USB. FIG. 22B depicts the reverse side of main PCB 2200 with an exemplary MEA assembly 2205 disposed through void 2203 such that the cell cultivation surfaces of the MEA assembly are oriented in the same direction as the reverse side of the main PCB and the MEA assembly is in electrical contact with contacts 2204. FIG. 22C depicts an image sensor 2206 engaged with MEA assembly 2205. In some embodiments, main PCB 2200, MEA assembly 2205, and image sensor 2206 are assembled as pictured in FIG. 22C and then inserted into a faraday cage to reduce external noise. In some embodiments, the faraday cage is substantially rectangular, with an open top. The complete assembly is sized to be placed inside an existing incubator. In this way, consistent environmental control is provided, and a plurality of modular assemblies as herein disclosure may be maintained in parallel. In some embodiments, an array of modular assemblies is provided, wherein individual assemblies may be inserted or removed individually from a shared incubator.

In an exemplary embodiment of the present disclosure, an apparatus for measuring conduction velocity of cells is provided. A microelectrode array is operatively coupled to an amplifier. Output signals of the microelectrode array are amplified by the amplifier. A battery is operatively coupled to the amplifier. The battery provides power to the amplifier. An analog to digital converter is operatively coupled to the amplifier. The amplifier is electrically isolated from the analog to digital converter by at least one opto-isolator. An output interface is operatively coupled to the analog to digital converter. In some embodiments, the microelectrode array is disposed within a faraday cage.

While the disclosed subject matter is described herein in terms of certain exemplary embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

What is claimed is:

1. A microelectrode array for measuring conduction velocity of cells, comprising:
    a substantially flat substrate including a first surface and a second surface;
    a plurality of measurement electrodes arrayed on the first surface of the substrate, each electrode including a contact portion and a non-contact portion, wherein the contact portions of the plurality of measurement electrodes are aligned along a single straight line within the uncovered region, forming a linear configuration on the first surface of the substrate;
    a coating covering a portion of the first surface of the substrate and the non-contact portions of the electrodes so as to form a covered and an uncovered region, wherein the uncovered region is substantially rectangular, having a length and a width, the width being from 50 µm to 300 µm;
    wherein the first surface comprises one or more regions of patterned and nonpatterned glass areas wherein the nonpatterned area is chemically modified to provide preferential cell attachment to provide micropatterning of cells within the uncovered region;
    a mold disposed on the first surface of the substrate, having at least one cell culture well penetrating the body of the mold to expose the microelectrode array in the uncovered region;
    an imaging sensor disposed on the second surface of the substrate; whereby the microelectrode array is disposed between the mold and the imaging sensor;
    wherein the plurality of measurement electrodes are configured to output a signal corresponding to cardiac action potential of the cells at multiple points along the linear configuration and the imaging sensor is configured to simultaneously acquire optical data of the cells.

2. The microelectrode array of claim 1, wherein the substrate is transparent.

3. The microelectrode array of claim 1, wherein the substrate comprises a glass slide.

4. The microelectrode array of claim 1, wherein the coating comprises silica.

5. The microelectrode array of claim 1, wherein the plurality of measurement electrodes comprise gold.

6. The microelectrode array of claim 1, wherein the plurality of measurement electrodes comprise gold and titanium.

7. The microelectrode array of claim 1, wherein the plurality of measurement electrodes comprise indium tin oxide.

8. The microelectrode array of claim 1, wherein the plurality of measurement electrodes are deposited on the first surface of the substrate by electron beam physical vapor deposition.

9. The microelectrode array of claim 1, wherein the plurality of measurement electrodes are deposited on the first surface of the substrate by sputter deposition.

10. The microelectrode array of claim 1, wherein the coating is deposited on the first surface of the substrate and the non-contact portions of the electrodes by electron beam physical vapor deposition.

11. The microelectrode array of claim 1, wherein the coating is deposited on the first surface of the substrate and the non-contact portions of the electrodes by sputter deposition.

12. The microelectrode array of claim 1, further comprising a plurality of cells aligned and elongated within the uncovered region.

13. The microelectrode array of claim 12, wherein the plurality of cells includes cardiac cells, the cardiac cells comprising cardiac myocytes.

14. The microelectrode array of claim 1, wherein the plurality of measurement electrodes comprises a plurality of pairs, each pair being closer to each other on the first surface than to the other pairs.

15. The microelectrode array of claim 1, wherein the contact portions of the plurality of measurement electrodes are substantially evenly spaced along the linear configuration within the uncovered region.

16. The microelectrode array of claim 1, further comprising a protein layer disposed in the uncovered region only in the cell attachment region.

17. The microelectrode array of claim 16, wherein the protein layer comprises fibronectin.

18. The microelectrode array of claim 1 wherein the ratio of the length to the width being from three to ten.

19. The microelectrode array of claim 1 comprising a plurality of uncovered regions, wherein the uncovered regions are substantially rectangular, having a length and a width, the ratio of the length to the width being from three to ten and the width being from 50 µm to 300 µm.

20. The microelectrode array of claim 1 wherein the linear configuration of the electrodes is parallel to the length of the uncovered region.

21. The microelectrode array of claim 1 configured to measure electrical and calcium signals simultaneously.

22. The microelectrode array of claim 21 configured to allow for image analysis of cell contraction or cellular fluxes due to tracking of fluorescent calcium or voltage dyes.

23. The microelectrode array of claim 13 further comprising fibroblasts.

24. The microelectrode array of claim 23 comprising cells patterned to provide differing percentages of cardiac myocytes and fibroblasts within the uncovered region.

25. The microelectrode array of claim 24 comprising cells patterned to provide conduction blocks comprising aggregates of fibroblasts.

* * * * *